US012644858B2

(12) United States Patent
Tabib-Azar

(10) Patent No.: US 12,644,858 B2
(45) Date of Patent: Jun. 2, 2026

(54) METHODS FOR REDUCING ELECTRODE GAP DISTANCES IN ELECTRONIC DEVICES AND RESULTING DEVICES HAVING NANOMETER ELECTRODE GAPS VIA LIQUID PHASE MOLECULAR LAYER DEPOSITION TECHNIQUE

(71) Applicant: University of Utah Research Foundation, Salt Lake City, UT (US)

(72) Inventor: Massood Tabib-Azar, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 966 days.

(21) Appl. No.: 17/770,969

(22) PCT Filed: Oct. 26, 2020

(86) PCT No.: PCT/US2020/057300
§ 371 (c)(1),
(2) Date: Apr. 21, 2022

(87) PCT Pub. No.: WO2021/081478
PCT Pub. Date: Apr. 29, 2021

(65) Prior Publication Data
US 2022/0397546 A1 Dec. 15, 2022

Related U.S. Application Data

(60) Provisional application No. 63/021,605, filed on May 7, 2020, provisional application No. 62/926,376, filed on Oct. 25, 2019.

(51) Int. Cl.
*G01N 27/414* (2006.01)
*G01N 15/01* (2024.01)
(Continued)

(52) U.S. Cl.
CPC ..... *G01N 27/4145* (2013.01); *G01N 15/0637* (2013.01); *G01N 27/4146* (2013.01);
(Continued)

(58) Field of Classification Search
CPC ........... G01N 27/4145; G01N 15/0637; G01N 27/4146; G01N 33/54373; G01N 33/5438;
(Continued)

(56) References Cited

U.S. PATENT DOCUMENTS 6,458,327 B1    10/2002  Vossmeyer
6,515,325 B1     2/2003  Farnworth et al.
(Continued)

FOREIGN PATENT DOCUMENTS

CN        107525929 A    10/2019
CN        110297028 A    10/2019
(Continued)

OTHER PUBLICATIONS

Azizah, Gold nanoparticle mediated method for spatially resolved deposition of DNA on nono-gapped interdigitated electrodes, and it's application to the detection of the human Papillomavirus, Oct. 6, 2016, Microchimica Acta, vol. 183, pp. 3119-3126, Austria.
(Continued)

*Primary Examiner* — Charles Capozzi
*Assistant Examiner* — Jacqueline Brazin
(74) *Attorney, Agent, or Firm* — Thorpe North & Western, LLP

(57) ABSTRACT

A method for reducing electrode gap distances in an electronic device having a first electrode spatially separated from a second electrode by an electrode gap can comprise selecting (810) a milometer gap size to bind a biological material based on a size of the biological material and binding effects with the biological material. The method can
(Continued)

further comprise coating (820) at least one surface of an electrode gap region with a first layer including molecular recognition groups, and coating (830) the at least one surface with a second layer including electrically-conductive solids that are configured to bond with the molecular recognition groups. The electronic device can be further coated (840) with additional alternating layers of the molecular recognition groups and the electrically-conductive solids to reach the nanometer gap size between a first electrode and a second electrode of the electronic device.

23 Claims, 26 Drawing Sheets

(51) Int. Cl.

| | |
|---|---|
| *G01N 15/06* | (2024.01) |
| *G01N 33/543* | (2006.01) |
| *G01N 33/569* | (2006.01) |
| *G06N 20/00* | (2019.01) |
| *G16H 50/20* | (2018.01) |

(52) U.S. Cl.
CPC ... *G01N 33/54373* (2013.01); *G01N 33/5438* (2013.01); *G01N 33/56983* (2013.01); *G06N 20/00* (2019.01); *G16H 50/20* (2018.01); *G01N 15/01* (2024.01); *G01N 2333/165* (2013.01); *G01N 2333/185* (2013.01)

(58) Field of Classification Search
CPC ............. G01N 33/56983; G01N 15/01; G01N 2333/165; G01N 2333/185; G01N 27/3278; G06N 20/00; G16H 50/20; B82Y 15/00
USPC ...................................................... 435/287.2
See application file for complete search history.

(56) References Cited

U.S. PATENT DOCUMENTS

| | | |
|---|---|---|
| 6,569,630 B1 | 5/2003 | Vivekananda et al. |
| 7,056,748 B1 | 6/2006 | Braun et al. |
| 7,348,183 B2 | 3/2008 | Fritsch et al. |
| 7,485,453 B2 | 2/2009 | Cohen et al. |
| 7,602,496 B2 | 10/2009 | Harsh et al. |
| 8,247,197 B2 | 8/2012 | Sode et al. |
| 8,313,633 B2 | 11/2012 | Li et al. |
| 8,470,532 B2 | 6/2013 | Lu et al. |
| 8,691,500 B2 | 4/2014 | Kim et al. |
| 8,709,791 B2 | 4/2014 | Larson et al. |
| 8,898,069 B2 | 11/2014 | Hood et al. |
| 8,945,836 B2 | 2/2015 | Todd et al. |
| 9,068,216 B2 | 6/2015 | Barnhizer et al. |
| 9,128,101 B2 | 9/2015 | Halbert et al. |
| 9,303,292 B2 | 4/2016 | Shawky Abduo et al. |
| 9,610,037 B2 | 4/2017 | Baym et al. |
| 9,857,328 B2 | 1/2018 | Hoffman |
| 10,155,988 B2 | 12/2018 | Iqbal et al. |
| 10,168,315 B2 | 1/2019 | Haick et al. |
| 10,175,223 B2 | 1/2019 | Holt |
| 10,261,066 B2 | 4/2019 | Ikeda et al. |
| 10,426,857 B2 | 10/2019 | Boyden et al. |
| 10,545,161 B2 | 1/2020 | Khattak et al. |
| 10,585,094 B2 | 3/2020 | Mackay et al. |
| 10,605,761 B2 | 3/2020 | Xia et al. |
| 10,663,712 B2 | 5/2020 | Eshel et al. |
| 2003/0027327 A1 | 2/2003 | Cunningham et al. |
| 2004/0023253 A1 | 2/2004 | Kunwar et al. |
| 2004/0124084 A1 | 7/2004 | Fritsch et al. |
| 2005/0074871 A1 | 4/2005 | Albert et al. |
| 2005/0077179 A1 | 4/2005 | Rhodes |
| 2005/0116263 A1 | 6/2005 | Lu et al. |

| | | |
|---|---|---|
| 2008/0149479 A1 | 6/2008 | Olofsson et al. |
| 2008/0160638 A1 | 7/2008 | Lederman et al. |
| 2009/0117571 A1 | 5/2009 | Solanki et al. |
| 2009/0235746 A1 | 9/2009 | Mutharasan |
| 2009/0273354 A1 | 11/2009 | Dirani et al. |
| 2010/0135854 A1 | 6/2010 | Yang et al. |
| 2011/0053139 A1 | 3/2011 | Larson et al. |
| 2011/0120868 A1* | 5/2011 | Lindsay ............... C12Q 1/6869 |
| | | 216/13 |
| 2011/0171629 A1* | 7/2011 | Swager ............ G01N 33/54346 |
| | | 977/773 |
| 2011/0171749 A1 | 7/2011 | Alocilja et al. |
| 2012/0196384 A1 | 8/2012 | Zhang |
| 2013/0065777 A1 | 3/2013 | Altug et al. |
| 2013/0273522 A1 | 10/2013 | Lowery, Jr. et al. |
| 2014/0162893 A1 | 6/2014 | Haam et al. |
| 2015/0038361 A1 | 2/2015 | Erickson et al. |
| 2015/0056627 A1 | 2/2015 | Karkkainen et al. |
| 2015/0301058 A1 | 10/2015 | Schettini et al. |
| 2016/0122794 A1 | 5/2016 | Trenholm et al. |
| 2016/0300915 A1 | 10/2016 | Majima et al. |
| 2017/0015667 A1 | 1/2017 | Bowman et al. |
| 2017/0052174 A1 | 2/2017 | Branch et al. |
| 2017/0089899 A1 | 3/2017 | Kundrod et al. |
| 2017/0154164 A9 | 6/2017 | Levinson et al. |
| 2017/0168000 A1 | 6/2017 | Ichiki |
| 2017/0263874 A1 | 9/2017 | Isogai et al. |
| 2017/0350856 A1 | 12/2017 | Kobayashi et al. |
| 2018/0003712 A1 | 1/2018 | Cash et al. |
| 2018/0050058 A1 | 2/2018 | Kim et al. |
| 2018/0108440 A1 | 4/2018 | Stevens et al. |
| 2018/0216157 A1 | 8/2018 | Lamble et al. |
| 2018/0275028 A1 | 9/2018 | Saito et al. |
| 2018/0330056 A1 | 11/2018 | Stoughton et al. |
| 2019/0004003 A1 | 1/2019 | Merriman et al. |
| 2019/0034565 A1 | 1/2019 | Varughese |
| 2019/0094175 A1 | 3/2019 | Merriman et al. |
| 2019/0128853 A1 | 5/2019 | Wright |
| 2019/0232282 A1 | 8/2019 | Pierson et al. |
| 2019/0292580 A1 | 9/2019 | Fu et al. |
| 2019/0390243 A1 | 12/2019 | Lee et al. |
| 2020/0018749 A1 | 1/2020 | Smolak et al. |
| 2020/0096514 A1 | 3/2020 | Bhatia |
| 2020/0150120 A1 | 5/2020 | Willson et al. |
| 2020/0181720 A1 | 6/2020 | Abudayyeh et al. |
| 2021/0117636 A1 | 4/2021 | Lin et al. |

FOREIGN PATENT DOCUMENTS

| | | |
|---|---|---|
| EP | 3537138 | 9/2019 |
| JP | 2009156827 | 7/2009 |
| JP | 2013-050426 A | 3/2013 |
| KR | 20100063598 | 6/2010 |
| KR | 2019 0013454 A | 2/2019 |
| KR | 2019-0054740 A | 5/2019 |
| KR | 2019-0107518 A | 9/2019 |
| WO | WO 2005/043126 A2 | 5/2005 |
| WO | WO 2011/146825 A2 | 11/2011 |
| WO | WO 2015/088446 A1 | 6/2015 |
| WO | WO 2016/154034 A1 | 9/2016 |
| WO | WO 2017/180745 A1 | 10/2017 |
| WO | WO 2019/145755 A1 | 8/2019 |
| WO | WO 2020/100159 A1 | 5/2020 |

OTHER PUBLICATIONS

Draz et al., Applications of gold nanoparticles in virus detection, Feb. 15, 2018, 62 pages, Theranostics, Denver, Colorado, doi:10.7150/thno.23856.

Khan et al., Lab-on-a-Chip Systems for Aptamer-Based Biosensing, Feb. 20, 2020, 30 Pages, MPDI Basel, Switzerland.

Written Opinion for International Application Serial No. PCT/US2020/057300 dated Jan. 26, 2021, 44 pages, United States.

Cesewiski et al., Electrochemical biosensors for pathoget detection, Online, http://www.elsevier.com/locate/bios, Oct. 6, 2019, 30 pages, Blacksburg, VA, doi.org/10.1016/j.bios.2020.112214.

(56) References Cited

OTHER PUBLICATIONS

DiLoria et al., Designer Surfaces for the Quantification of Multivalent Biological Interactions, Dissertation, Sep. 2019, University of Twente, 179 pages, Italy, doi.org/10.1016/j.bios.2020.112214.

Dolai et al., Terahertz Detaction of Zika Viruses, Feb. 2020, Preprints.org, 7 pages, Basel Switzerland, doi:10.20944/preprints202002.0232.v1.

Ghobaei et al., A label-free aptamer-based nanogap capacitive biosensor with greatly dimished electrode polarization effects, Royal Society of Chemistry, Aug. 2018, 11 pages, London, England, DOI: 10.1039/c8cp05510f.

Llgu et al., Aptamers for Diagnostics with Applications for Infectious Diseases, IntechOpen, 32 pages, London, England,DOI: http://dx.doi.org/10.5772/intechopen.84867.

Krejcova et al., Nanoscale virus biosensors: state of the art, Aug. 2015, Dove Press Journal, 20 pages, New Jersey, United States, doi.org/10.2147/NDD.S56771.

Kuitio et al. Aptamer-Based QCM-Sensor for Rapid Detection of PRRS Virus, Nov. 2018, MPDI, Basel, Switzerland.

Ravina et al., Detection methods for influenza A H1N1 virus with special reference to biosensors: a review, Nov. 2019, Portland Press, 18 pages, Utah, United States, doi.org/10.1042/BSR20193852.

Vand Den Kieboom et al., Trends in Analytical Chemistry, 2015, Elsevier B.V., Trends in Analytical Chemistry 74 (2015) pp. 58-67, Elsevier, United Kingdom.

Zou et al., (2019) Application of Aptamers in Virus Detection and Antiviral Therapy, Front. Microbiol. 10:1462., doi: 10.3389/fmicb.2019.01462.

Written Opinion for International Application Serial No. PCT/US20/57190 dated Dec. 28, 2020, 90 pages, United States.

Basu et al., Microelectromechanical Resonators for Radio Frequency Communication Applications, Department of Electronics and Electrical Communication Engineering Indian Institute of Technology Kharagpur, Oct. 2011, vol. 17 (Oct. 2011), pp. 1557-158040 pages, West Bengal, India, DOI: 10.1007/s00542-011-1332-9.

Lang et al., Vantilever array sensors, National Competence Center for Research, Apr. 2005, 7 pages, Basel, Switzerland.

Namhil et al., Phys. Chem. Chem. Phys,. 2018, 25 pages, DOI:10.1038/C8CP05510F.

Saylan et al., An Alternative Medical Diagnosis Method: Biosensors for Virus Detection, Mar. 2019, MDPI, 22 pages, Basel, Switzerland, doi:10.3390/bios9020065.

Ho Bin Seo et al., Aptamer-based sandwich-type biosensors, Advanced Biology-Inspired Engineering, 2017, 7 pages, Cambridge, MA, United States DOI 10.1186/s13036-017-0054-7.

Kirkegaard, Aptasensor development for detection of virus in water, DTU Library, 2016, 2015 pages, Michigan, United States.

Kumar, Monitoring Intact Viruses Using Aptamers, National Institute of Advanced Industrial Science and Technology, Jul. 2016, Ibaraki, Japan.

Labib et al., Electrochemical Aptasensors for Microbial and Viral Pathogens,Springer Heidelberg 2013, pp. 155-181, Berlin Germany, DOI: 10.1007/10_2013_229.

Lee et al., An Aptamer-Based Electrochemical Sensor That Can Distinguish Influenza Virus Subtype H1 from H5, J. Microgiol. Biotechnol, 2017, vol. 27(11), pp. 2037-2043, Korea, doi.org/10.4014/jmb.1708.08015.

Tanchorean et al., Electrochemical Biosensor Based on Surface Imprinting for Zika Virus Detection in Serum, American Chemical Society Publications, Aug. 2018, 7 pages, Washington D.C., DOI: 10.1021/acssensors.8b00885.

Ruslinda, et al., Effects of Diamond-FET-based RNA aptamer sensing for detection of real sample of HIV-1 Tat protein, Biosensors and Bioelectronics, 2013, vol. 40, pp. 277-282, Amsterdam, The Netherlands.

Written Opinion for International Application Serial No. PCT/US20/57375 dated Mar. 10, 2021, 77 pages, United States.

Polo-Guisan, Immobilization of Enzymes and Cells, Humana Press, Library of Congress Control No. 2013944230, 27 pages, London, England, DOI 10.1007 /978-1-62703-550-7.

Saylan, An Alternative Medical Diagnosis Method: Biosensors for Virus Detection, Mar. 2019, MDPI, 22 pages, Basel, Switzerland, doi:10.3390/bios9020065.

Tiwari et al., Functionalized Gold nanoparticles and Their Biomedical Applications, Mar. 2011, Open Access Nanomaterials, 33 pages, Alabama, United States.

Arima et al., Selective Detections of Aingle-Viruses Using Solid-State Nanopores, Scientific Reports, Nov. 2018, 7 pages, United Kingdom, DOI:10.1038/s41598-018-34665-4.

Astill et al., Detecting and Predicting Emerging Disease in Poultry With the Implementation of New Technologies and Big Data: A Focus on Avian Influenza Virus, Frontiers in Veterinary Science, Oct. 2018, 12 pages, Switzerland, doi: 10.3389/fvets.2018.00263.

Chang et al., Artificial Intelligence in Pathology, Journal of Pathology and Translational Medicine, 2016 vol. 53 1-12, South Korea. doi.org/10.4132/jptm.2018.12.16.

Hastings, Nanopore Sensor Exploits Artificial Intelligence for Specific Virus Detection, Medgadget, Nov. 2018, California, United States.

Lessen et al., Real-Time Virus Size Classification Using Surface Plasmon PAMONO Resonance and Convolutional Neural Networks, Department of Computer Science VII, 2 pages, Germany.

Siedhoff, A Parameter-Optimizing Model-Based Approach to the Analysis of Low-SNR Image Sequences for Biological Virus Detection, Disertation, 2016, Germany.

Written Opinion for International Application Serial No. PCT/US20/57384 dated Mar. 25, 2021, 20 pages, United States.

Written Opinion for International Application Serial No. PCT/US20/57289 dated Jan. 22, 2021, 13 pages, United States.

Dolai et al., Zika Virus Field Effect Transistor; IEEE Sensors Journal, vol. 21, No. 4, Feb. 15, 2021, pp. 4122-4128.

Kasap et al., Biosensors Based on Nano-Gold/Zeolite-Modified lon Selective Field-Effect Transistors for Creatinine Detection, Nanoscale Research Letters, DOI 10.1186/s11671-017-1943-x, 2017, 11 pages.

Tsai et al., Electrical detection of DNA hybridization with multilayer gold nanoparticles between nanogap electrodes, Microsystem Technologies 11 (2005), DOI 10.1007/s00542-004-0436-x, pp. 91-96.

Kim et al., An Underlap Channel-Embedded Field-Effect Transistor for Biosensor Application in Watery and Dry Environment, IEEE Transactions on Nanotechnology, vol. 11, No. 2, 2012, pp. 390-394.

Yang et al., Zika virus detection using antibody-immobilized disposable cover glass and AlGaN/GaN high electron mobility transistors, Applied Physics Letters, Research Article, 2018, 6 pages.

Boisen et al., Rapid molecular detection of food- and water-borne diseases, Microbilogy Today, 2007, 3 pages.

* cited by examiner

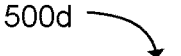
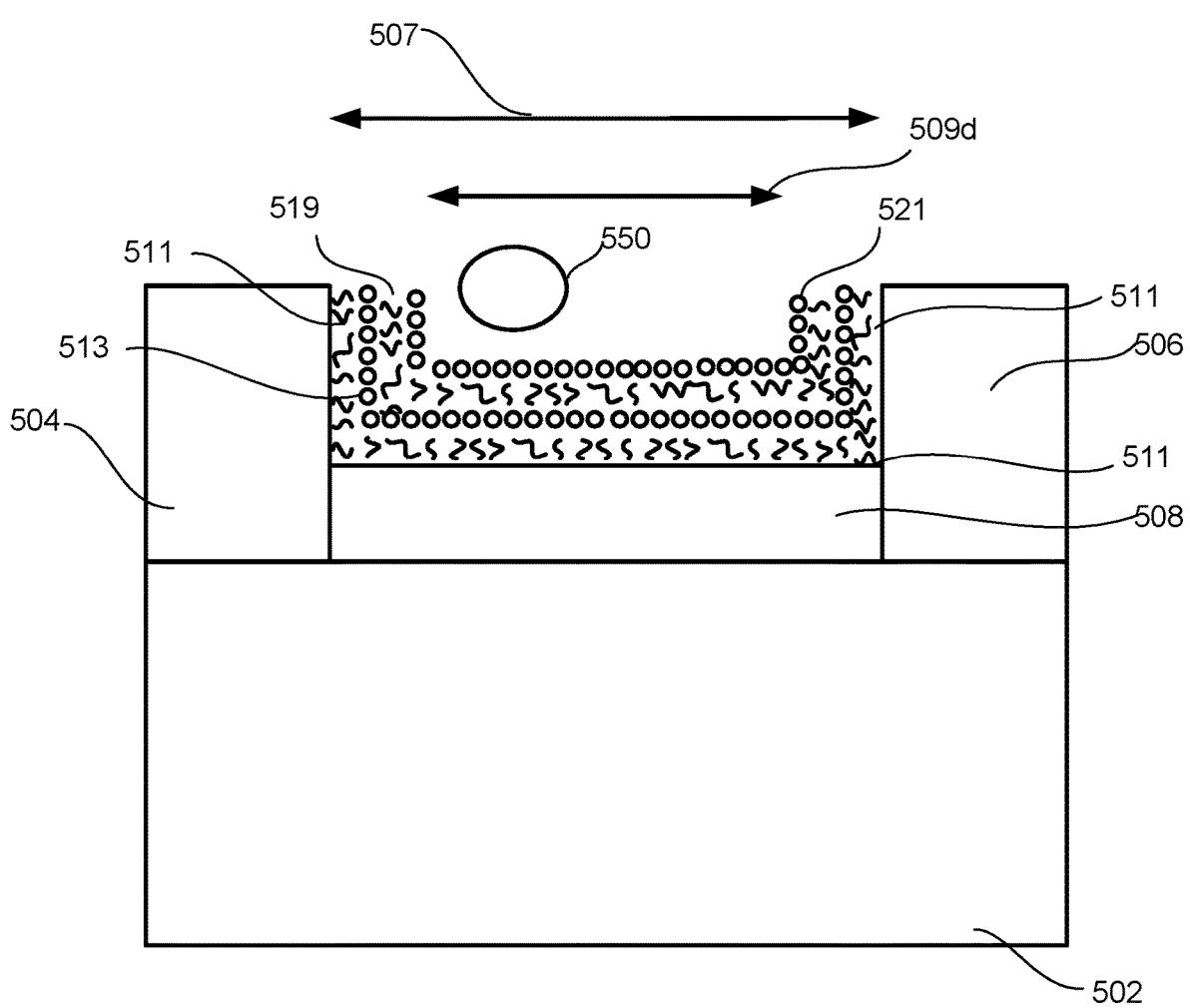
FIG. 5d

600

610

640

620

630

800

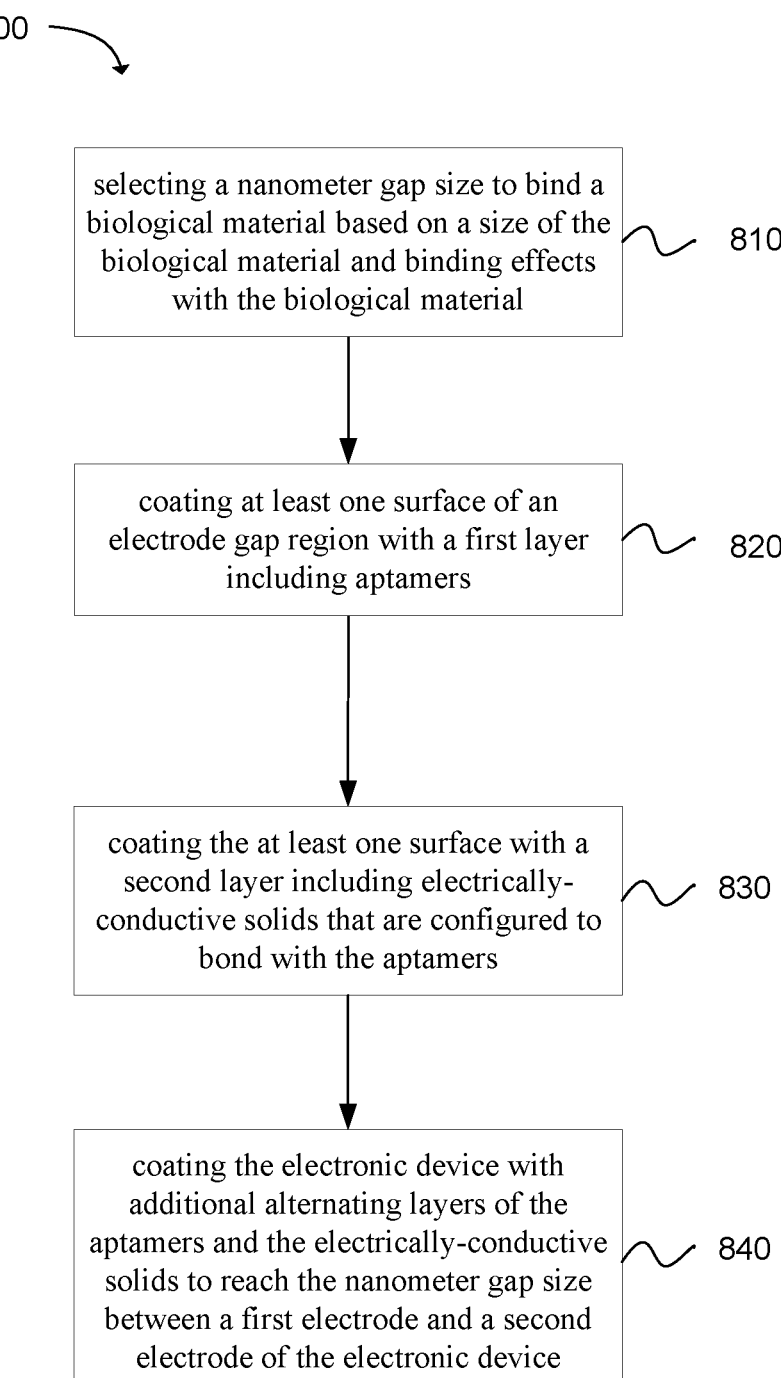

selecting a nanometer gap size to bind a biological material based on a size of the biological material and binding effects with the biological material — 810 coating at least one surface of an electrode gap region with a first layer including aptamers — 820 coating the at least one surface with a second layer including electrically-conductive solids that are configured to bond with the aptamers — 830 coating the electronic device with additional alternating layers of the aptamers and the electrically-conductive solids to reach the nanometer gap size between a first electrode and a second electrode of the electronic device — 840

FIG. 8

METHODS FOR REDUCING ELECTRODE GAP DISTANCES IN ELECTRONIC DEVICES AND RESULTING DEVICES HAVING NANOMETER ELECTRODE GAPS VIA LIQUID PHASE MOLECULAR LAYER DEPOSITION TECHNIQUE

RELATED APPLICATION

This application claims priority to U.S. Provisional Application No. 62/926,376 filed Oct. 25, 2019 and U.S. Provisional Application No. 63/021,605 filed May 7, 2020, which are each incorporated herein by reference.

GOVERNMENT INTEREST

This invention was made with government support under grant no. 1931100 awarded by the National Science Foundation. The government has certain rights in the invention.

FIELD OF THE INVENTION

The present invention relates to methods for reducing electrode gap distances in an electronic device and devices related thereto. Therefore, the present invention relates generally to the fields of material science, chemistry, nanomanufacturing, sensors (including biosensors), actuators and electronics.

BACKGROUND

Nanolithography relates to the patterning, formation, etching or bottom-up deposition of nanometer-scale structures by etching or depositing materials to form structures with nanometer feature sizes at least in two dimensions.

Nanolithography can be a very expensive process that uses advanced lithography tools, mask making, and related processes and materials that are a significant economic concern for industry. For example, the cost to build facilities that can adequately utilize nanolithography can be billions of dollars. Lithography techniques with patterning below 10 nm further enhance the functionality of the integrated electronic circuits and sensors/actuators but at the same time exponentially increases the complexity and manufacturing challenges.

Submicroscopic, often nanometer scale infectious agents, such as viral proteins, RNA, DNA and viruses, have played a significant role in common diseases and in globally affecting the world health. Detecting infectious agents using devices with nanometer-scale active areas matched with the dimensions of the viral particles is becoming a very powerful area of detection and identification area of research and development with the potential to diagnose, treat, mitigate, and prevent the spread of these infectious diseases. However, the expense associated with using nanolithography has deterred the development of cost-effective suitable nanoscale biological sensors.

SUMMARY

Methods for reducing electrode gap distances in electronic devices, sensors and actuators and the electronic devices related thereto can facilitate the development of low-cost devices that can detect viruses and other submicroscopic biological materials without using expensive nanolithography. More generally, the methods disclosed herein can allow formation of micrometer-scale devices with nanometer-scale active region and features. As a frame of reference, more recently developed quantum mechanical tunneling current whole virus sensors include a small gap between electrodes. This gap can be used to as a detection region where virus or other biological material can be oriented to change electronic responses of the device, e.g. voltage, current, capacitance, resistance, tunneling effects, etc. The size of the gap can also effect performance and selectivity for a particular viral particles or nanoparticles in general.

In one embodiment, a method for reducing electrode gap distances in an electronic device having a first electrode spatially separated from a second electrode by an electrode gap can comprise determining a nanometer gap distance which corresponds to a desired gap distance which is smaller than an initial electrode gap distance. The desired nanometer gap distance is chosen based on a target biological material (e.g. virus, DNA, RNA, viral proteins, etc.) to be detected and can be a function of a size of the biological material and binding effects with the biological material. The method can further comprise coating at least one surface of an electrode gap region with a first layer including molecular recognition groups which selectively bind to the at least one surface. The at least one surface and/or the molecular recognition groups can be functionalized or otherwise prepared to bond with one another to form the first layer of molecular recognition group. The method can further comprise coating the first layer of molecular recognition group with a second layer including electrically-conductive solids that are configured to bond with the molecular recognition groups. Typically, surfaces other than the at least one surface are either chosen or coated to prevent bonding with either the molecular recognition group or the electrically-conductive solids. The method can further comprise coating the electronic device with additional alternating layers of the molecular recognition groups and the electrically-conductive solids to reach the desired nanometer gap distance between the first electrode and the second electrode of the electronic device.

Corresponding devices formed by the above methods are also described. For example, a micrometer-scale device can comprise a first electrode and a second electrode separated by an electrode gap. The first electrode can include alternating layers of coated molecular recognition groups and coated electrically-conductive solids. The second electrode can also include alternating layers of coated molecular recognition groups and coated electrically-conductive solids. As a result of these alternating layers the electrode gap is reduced to a nanometer gap size between the first electrode and the second electrode.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure.

FIG. 5d is a side view illustrating a method for reducing electrode gap distances in an electronic device having a first electrode spatially separated from a second electrode by an electrode gap in accordance with an example.

FIG. 8 is a flowchart depicting a method for reducing electrode gap distances in an electronic device in accordance with an example.

Figure 1A:
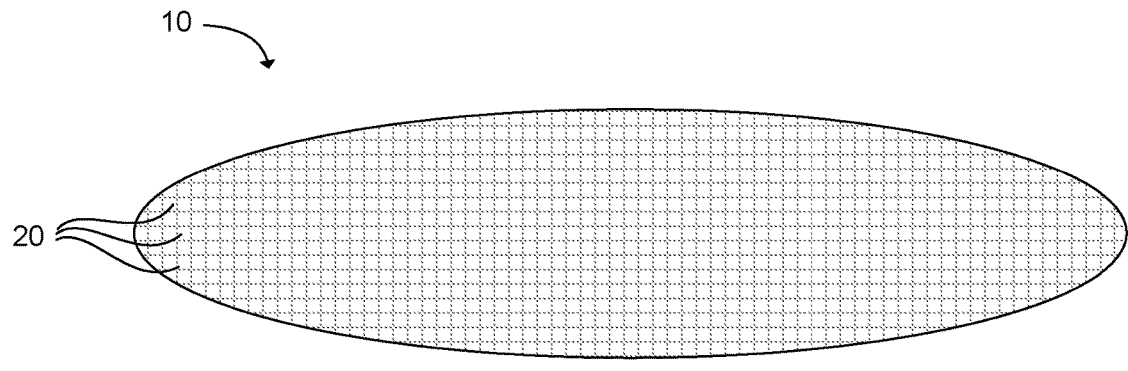
FIG. 1a is a top perspective view of a wafer including an array of sensor devices formed on corresponding die elements in accordance with one example.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Assembly of Nanometer-Scale Molecules in Micrometer-Scale Devices

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

A method for reducing electrode gap distances in an electronic device having a first electrode spatially separated from a second electrode by an electrode gap can comprise determining a nanometer gap size which corresponds to a desired gap distance which is smaller than an initial electrode gap distance. The desired nanometer gap distance is chosen based on a target biological material (e.g. virus, DNA, RNA, viral proteins, etc.) to be detected and can be a function of a size of the biological material and binding effects with the biological material. The method can further comprise coating at least one surface of an electrode gap region with a first layer including molecular recognition groups which selectively bind to the at least one surface. The at least one surface and/or the molecular recognition groups can be functionalized or otherwise prepared to bond with one another to form the first layer of molecular recognition group. The method can further comprise coating the first layer of molecular recognition group with a second layer including electrically-conductive solids that are configured to bond with the molecular recognition groups. Typically, surfaces other than the at least one surface are either chosen or coated to prevent bonding with either the molecular recognition group or the electrically-conductive solids. The method can further comprise coating the electronic device with additional alternating layers of the molecular recognition groups and the electrically-conductive solids to reach the desired nanometer gap distance between the first electrode and the second electrode of the electronic device.

Corresponding devices formed by the above methods are also described. For example, a micrometer-scale device can comprise a first electrode and a second electrode separated by an electrode gap. The first electrode can include alternating layers of coated molecular recognition groups and coated electrically-conductive solids. The second electrode can also include alternating layers of coated molecular recognition groups and coated electrically-conductive solids. As a result of these alternating layers the electrode gap is reduced to a nanometer gap size between the first electrode and the second electrode.

As illustrated in FIG. 1a, the nanogap formation processes described herein can be applied across a whole wafer 10. Consistent with standard device formation, an array of devices 20 can be formed on a single wafer and then later segmented into individual die which can be mounted on a circuit board or other substrate for integration into a final device. Thus, in one example, all the devices 20 on the wafer 10 can be processed in parallel simultaneously.

Figure 1B:
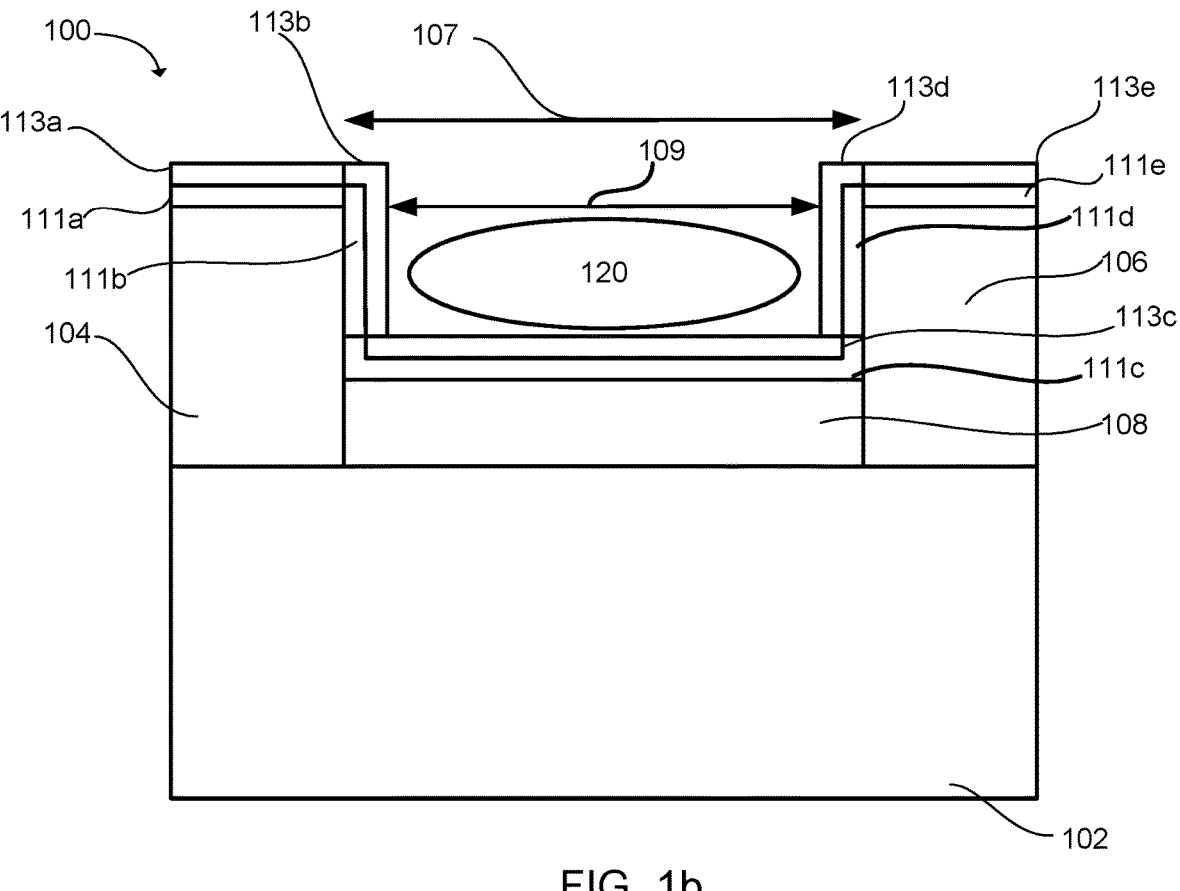
FIG. 1B is a side view illustrating an electronic device with a nanometer gap size in accordance with an example.

In one embodiment, as illustrated with reference to FIG. 1B, a method for reducing electrode gap distances 107 in an electronic device 100 having a first electrode 104 spatially separated from a second electrode 106 by an electrode gap 107 can include selecting a nanometer gap size 109 to bind a biological material 120 based on a size of the biological material and binding effects with the biological material. In one aspect, the method can further include coating at least one surface of an electrode gap 107 region with a first layer (e.g., 111a, 111b, 111c, 111d, and 111e) including molecular recognition groups. In another aspect, the method can further include coating the at least one surface with a second layer (e.g., 113a, 113b, 113c, 113d, and 113e) including electrically-conductive solids that can be configured to bond with the molecular recognition groups. In another aspect, the method can further include coating the electronic device 100 with additional alternating layers of the molecular recognition groups and the electrically-conductive solids to reach the nanometer gap size 109 between a first electrode 104 and a second electrode 106 of the electronic device 100. In one aspect, the electronic device 100 can include a support substrate 102 and a channel 108. In one aspect, the electronic device 100 can be a sensor based on a field-effect transistor or an electron tunneling device. Thus, if the device is not configured as an FET, then channel 108 can alternatively be a dielectric or insulating material, or other suitable material depending on the device design.

In one aspect, the at least one surface can be each of the first electrode 104 and the second electrode 106 and a channel 108 surface oriented between the first electrode 104 and the second electrode 106. In other words, in some cases, the alternating layers can be formed only on inner electrode sides facing one another (i.e. 111b, 111d), and alternatively also on a bottom surface of the electrode gap region.

In another aspect, the first layer (e.g., 111a, 111b, 111c, 111d, and 111e) and the second layer (e.g., 113a, 113b, 113c, 113d, and 113e) can be monolayers. When the layer including molecular recognition groups is a monolayer, the layer can have a thickness of a single molecule. When the layer including electrically-conductive solids is a monolayer, the layer can have having a thickness of a single particle. The thickness of these layers can vary depending on the molecular recognition group and solids. However, as a general rule, aptamers can extend from about 10-100 nucleotides in length (i.e. about 3-30 nm). The aptamers can also be truncated to allow for removal of non-essential nucleotides which do not participate in binding and to allow for more careful tuning of the gap reduction distances. Similarly, the solid particles can be in the form of nanoparticles which can be readily provide in sizes ranging from about 1 nm to about 500 nm, and most often from about 10 nm to 100 nm. In another case, the solid particles can be in the form of microbeads having sizes from about 0.1 μm to about 100 μm. Such microbeads can be useful in reducing relatively larger gap sizes.

In one example, the biological material 120 can be at least one of a virus and a biomarker of the virus. In one aspect, the aptamers can be configured to selectively bind with the biological material 120.

Molecular recognition groups can be any chemical compound or group that selectively binds with the target virus. Non-limiting examples of molecular recognition groups can include aptamers, antigens, antibodies, and the like. Molecular recognition groups can generally include a surface bonding group and a virus binding group. Metal surfaces can be bonded with aptamers, antigens, antibodies, or other molecular recognition groups using any suitable functionalization technique. Further, metal surfaces can optionally be first prepared or activated via functionalization with an active group which binds with a corresponding end of the molecular recognition group. For example, a thiol group can be attached to the metal surface. However, in many cases, the molecular recognition group can include a surface bonding group which directly bonds to the metal surface. Non-limiting examples of surface bonding groups can include organosulfur thiols such as alkyl thiols, dialkyl disulfides, etc. Metal, e.g. gold, surface can also be functionalized via techniques such as, but not limited to, oligonucleotide functionalization via thiol groups, surface saturation with single stranded oligonucleotides, PEGylation optionally including thiol or azide bonding groups, photonic immobilization, azide functionalization, and the like. For some details on the known synthetic functionalization techniques, see INNOVACOAT Gold coatings; Polo E. et al. (2013) *Tips for the Functionalization of Nanoparticles with Antibodies*. In: Guisan J. (eds) Immobilization of Enzymes and Cells. Methods in Molecular Biology (Methods and Protocols), vol 1051. Humana Press, Totowa, N.J. pp. 149-163; Tiwari et al. Nanomaterials 2011, 1(1), 31-63, *Functionalized Gold Nanoparticles and Their Biomedical Applications*; which are each incorporated herein by reference. For example, thiols can be functionalized at one or both ends of an aptamer, an antigen, or an antibody.

Formation of each layer of molecular recognition groups and electrically-conductive solid particles can be performed using liquid phase deposition. For example, colloidal solutions of nanoparticles can be prepared and then drop cast onto the surface. Appropriate functionalization of the nanoparticles or molecular recognition groups can then result in bonding between the two. Residual unreacted materials can be removed by washing or evaporation. Similarly, a molecular recognition group (e.g. aptamer) solution can be applied to the surface or prior layer in order to bond with the surface or layer of solid conductive particles. The functionalized group can then react with the exposed conductive material (i.e. layer of conductive solid particles or electrode surface) to bind the molecular recognition groups to the conductive material.

In one aspect, the aptamers can include functional groups that are configured to selectively bind with the biological material 120. The aptamers can be obtained commercially or synthesized using known techniques such as SELEX (systemic evolution of ligands by exponential enrichment), RAPTAMER, and the like. Aptamers with different functional groups can be used to achieve varying degree of binding energies with molecules and surfaces. Water at a particular temperature can then be used to selectively separate certain molecules or the aptamers from different surfaces while leaving other surfaces and molecules un-altered based on differing binding energies. The particular temperature can be readily determined by testing the differential dissociation at different temperatures.

In one example, the biological material 120 can be a virus and the method can further include selecting the nanometer gap size 109 to bind a virus type based on a size of the virus type and binding effects with the virus type. In one example, the virus can be selected from the group consisting of: Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae (e.g. Zika), Orthomyxoviridae, Paramyxoviridae, Bunyaviridae, Rhabdoviridae, Filoviridae, Coronoviridae (e.g. SARS-CoV-2, SARS-CoV), Astroviridae, Bornaviridae, Arteriviridae, Hepeviridae, Retroviridae, Calimoviridae, Hepadnasviridae, the like, and combinations thereof. In another example, the virus type can be a subviral agent selected from the group consisting of: viroids, satellites, defective interfering particles, prions, the like, and combinations thereof.

In another aspect, the method can further include selecting the nanometer gap size 109 to bind the virus type based on the size of the virus type wherein the size of the virus type is less than at least one of: 500 nm, 450 nm, 400 nm, 350 nm, 300 nm, 250 nm, 200 nm, 150 nm, 100 nm, 75 nm, 50 nm, 35 nm, 20 nm, and 15 nm.

In one example, the biological material 120 can be a biomarker and the method can further include selecting the nanometer gap size 109 to bind the biomarker of the virus type based on the size of the biomarker and binding effects with the biomarker, wherein the biomarker has a biomarker size of less than at least one of 1 μm, 500 nm, 100 nm, 50 nm, 40 nm, 25 nm, and 15 nm. In one aspect, the biomarker can be an antibody for the virus type which are typically about 7 nm to 20 nm in size.

In another aspect, the method can include coating the electronic device 100 with the additional alternating layers to reach the nanometer gap size 109 less than at least one of: 1 μm, 900 nm, 800 nm, 700 nm, 600 nm, 500 nm, 450 nm, 400 nm, 350 nm, 300 nm, 250 nm, 200 nm, 150 nm, 100 nm, 75 nm, 50 nm, 35 nm, 20 nm, 15 nm, 10 nm, and 5 nm. In another aspect, the electrode gap before coating can be greater than at least one of: 1 μm, 5 m, 10 m, 20 μm, and 100 μm. Typically, the initial gap size can be defined with conventional optical photolithography resolutions around 1 μm.

In another aspect, the electrically conductive solids can include at least one of: carbon-based nanoparticles, metal nanoparticles, semiconductor nanoparticles, metal microbeads, semiconductor microbeads, and combinations thereof. In one aspect, the electrically conductive solids can include at least one of gold nanoparticles, silver nanoparticles, palladium nanoparticles, platinum nanoparticles, etc. and combinations thereof. Metallic nanoparticles can be selected for their ability to reduce the electrical resistance of the bridging layered structure in addition to their potentially other unique characteristics such as their catalytic and sensing characteristics. For example, palladium nanoparticles can be used to construct a very sensitive and selective hydrogen sensors. Or platinum nanoparticles can be used as a catalyst to lower energy required to react with hydrogen in the device.

In another embodiment, a micrometer-scale device 100 can include: (i) a first electrode 104 including alternating layers 111*a* and 111*b* and 113*a* and 113*b* of coated molecular recognition groups and coated electrically-conductive solids, (ii) a second electrode 106 including alternating layers 111*d* and 111*e* and 113*d* and 113*e* of coated molecular recognition groups and coated electrically-conductive solids, and (iii) a nanometer gap size 109 between the first electrode 104 and the second electrode 106. In one aspect, the nanometer gap size 109 can be reduced from a larger gap size 107 by the alternating layers (e.g., 111*a-e* and 1113*a-e*) of the coated molecular recognition groups and the coated electrically-conductive solids. In one aspect, the micrometer-scale device 100 can be a sensor based on a field-effect transistor or an electron tunneling device.

In one aspect, each layer (e.g., 111*a-e* or 113*a-e*) of the alternating layers of the coated molecular recognition groups and the coated electrically-conductive solids can be a monolayer including a thickness having a single molecule for a layer of the coated molecular recognition groups or a single particle for a layer of the coated electrically-conductive solids.

In another aspect, the nanometer gap size 109 can be less than at least one of: 1 μm, 900 nm, 800 nm, 700 nm, 600 nm, 500 nm, 450 nm, 400 nm, 350 nm, 300 nm, 250 nm, 200 nm, 150 nm, 100 nm, 75 nm, 50 nm, 35 nm, 20 nm, 15 nm, 10 nm, and 5 nm. In another aspect, the larger gap size 107 can be greater than at least one of: 1 μm, 2 μm, 5 μm, 10 μm, 15 μm, 20 μm, 30 μm, 40 μm, 50 μm, 60 μm, 75 μm, 100 μm, 150 μm, 200 μm, 300 μm, 400 μm, and 500 μm.

In another example, the coated aptamers can be selected to bind with at least one of a virus type and a biomarker. In another example, the electrically-conductive solids can include at least one of: carbon-based nanoparticles, metal nanoparticles, semiconductor nanoparticles, metal micro-beads, semiconductor microbeads, the like, and combinations thereof. In another example, the electrically conductive solids can include at least one of: gold nanoparticles, silver nanoparticles, palladium nanoparticles, platinum nanoparticles, the like, and combinations thereof.

In one example, a method to assemble nanometer-scale molecules in electronics, optical, mechanical, and magnetic devices can have applications in sensors, molecular electronics, and energy efficient electronics. In one example, nanometer-scale molecules can be incorporated in various devices to achieve a specific functionality without otherwise using nanometer scale device gaps or other features. Although nanolithography has been used to fabricate devices with nanometer receiving regions to assemble molecules, with this technique nanometer scale molecules can be assembled inside micrometer-scale gaps without using expensive nanolithography.

In one example, different types of chemically active molecules can be used to assemble specific functional molecules via a layer-by-layer additive technique. The molecules used as connection and assembly blocks can have specific functionalities enhancing mechanical, thermal, optical, magnetic, and electromagnetic functionalities of the overall device. Consequently, sophisticated nanodevices can be developed using convenient glassware technologies. For example, the first layer and any non-surface layers can be formed of oligonucleotides, polyethylene glycols, or other suitable extender molecules which reduce gap distance. The final and outermost layer can include aptamers. Regardless, each extender molecule can be bonded with the surface of the electrode gap and/or intermediate electrically-conductive solids.

Although some materials can bond directly with others, conductive surfaces, extender molecules, and/or aptamers can be functionalized in order to allow bonding as illustrated. Aptamers can generally include a surface bonding group and a virus binding group. Metal surfaces can be bonded with aptamers using any suitable functionalization technique. Further, metal surfaces can optionally be first prepared or activated via functionalization with an active group which binds with a corresponding end of an aptamer. For example, a thiol group can be attached to the metal surface. However, in many cases, the aptamer can include a surface bonding group which directly bonds to the metal surface. Non-limiting examples of surface bonding groups can include organosulfur thiols such as alkyl thiols, dialkyl disulfides, amines, etc. Thiols are predominantly used when strong bonding with metallic surfaces is desired. Metal surfaces can also optionally be functionalized via techniques such as, but not limited to, oligonucleotide functionalization via thiol groups, surface saturation with single stranded oligonucleotides, PEGylation optionally including thiol bonding groups, and the like. For example, thiols can be functionalized at one or both ends of an aptamer. Di-thiol aptamers may be used when aptamers are used as intermediate layers between conductive solids. In this case, the di-thiol aptamers can also be short and relatively stiff sufficient to reduce chances that both thiol ends will bond with the same surface. As another example, an intermediate molecule can be used to bond a virus binding end and create a link to bond with conductive solids. For example, C60 may be bonded with the virus binding end of a first layer of aptamer, followed by a second layer of aptamer bonded to the C60 at the virus binding group. In this case the free end of the aptamer in the second layer would be the functional surface bonding group which can then be bonded with a layer of electrically-conductive solids. Such intermediate and extender molecules can be repeated a sufficient number of times to form the desired nanogap distance. It is noted that throughout the description, aptamers are exemplified as the molecular recognition groups; however, each instance described can also utilize antibodies or antigens using the same principles described.

Figure 2A:
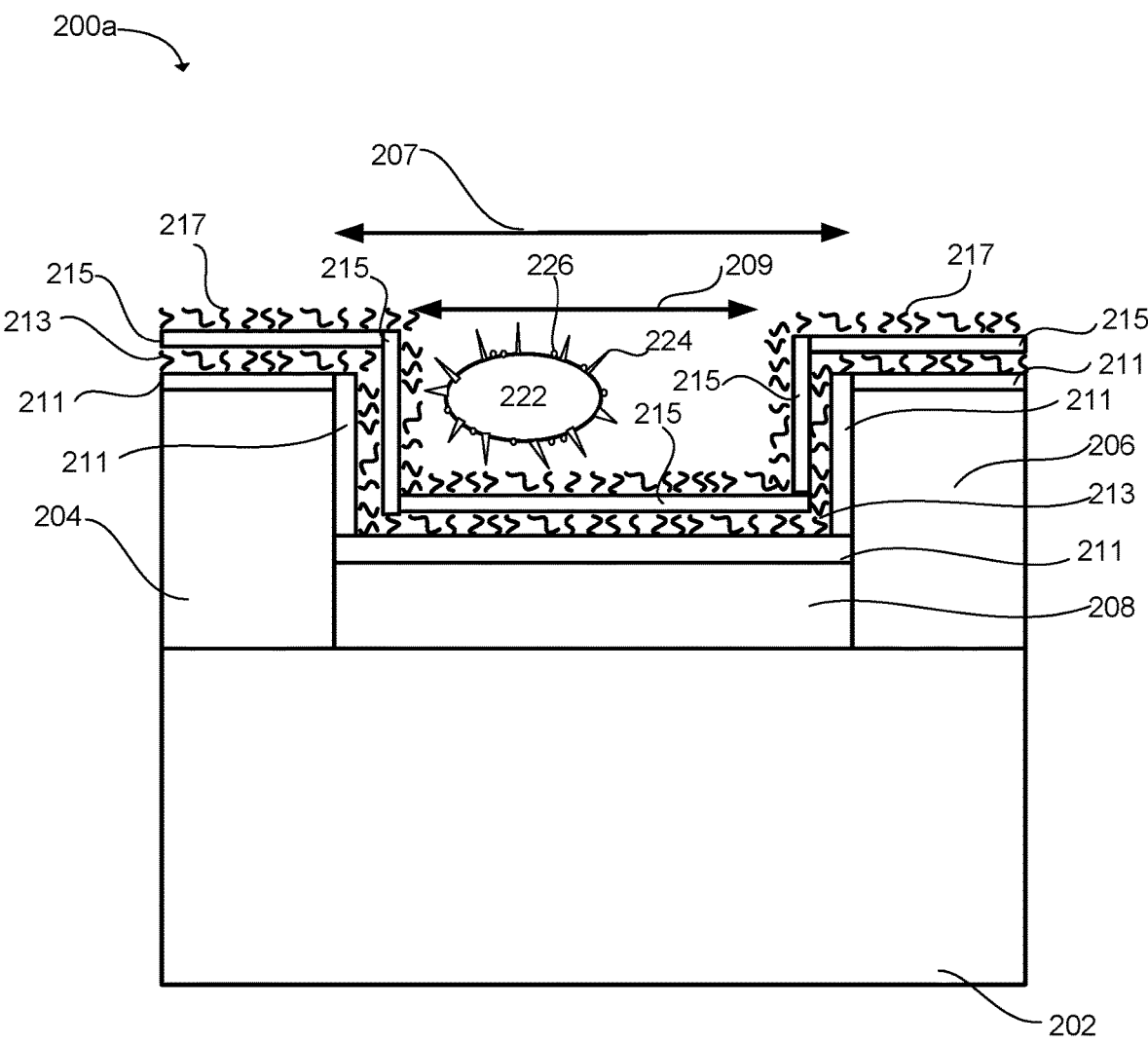
FIG. 2a is a side view illustrating an electronic device with a nanometer gap size selected to bind a virus in accordance with an example.
Figure 2B:
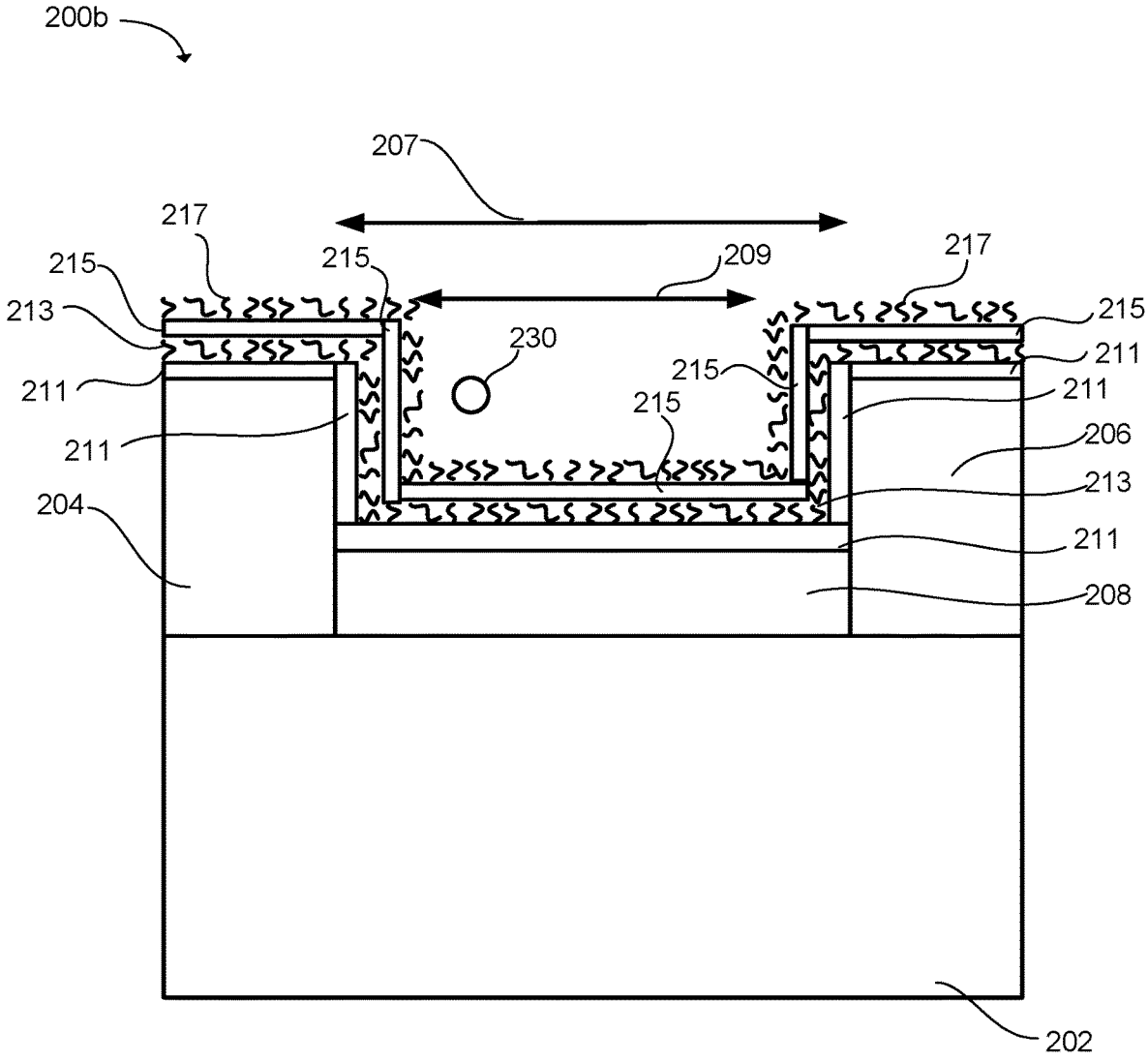
FIG. 2b is a side view illustrating an electronic device with a nanometer gap size selected to bind a biomarker in accordance with an example.

In another example, as illustrated in FIGS. 2a and 2b, a method for reducing electrode gap distances in an electronic device 200a or 200b can include a first electrode spatially separated from a second electrode by an electrode gap 207. In one aspect, a nanometer gap size 209 can be selected to bind a biological material, such as a virus 222, as illustrated in FIG. 2a, or a biological marker 230, as illustrated in FIG. 2b. The size of the nanometer gap size 209 can be based on the size of the biological material. In one example, when the nanometer gap size 209 is selected to bind to severe acute respiratory syndrome coronavirus 2 (SARS-CoV-2), the nanometer gap size 209 can be about 50 nm to about 90 nm. In another example, when the nanometer gap size 209 is selected to bind to biomarkers 230 or antibodies, the nanometer gap size 209 can be from about 2 nm to about 5 nm. There are many other applications of nano-meter scale gap sizes in generating near-fields through sub-wavelength openings, gas sensors based on direct electron spectroscopy of the physisorbed surface gas layers, etc. Thus, in these alternatives, the electrode gap and electrodes are replaced by corresponding sub-wavelength openings and gas sensor gaps. In these cases, the gap opening can be defined by non-electrically conducting materials or conductive materials.

In another aspect, the method can include selecting the nanometer gap size 209 based on binding effects with the biological material 222 or 230. In one example, when the nanometer gap size 209 is selected to bind to SARS-CoV-2, the binding effects with SARS-CoV-2 can include binding effects with the spike (S) protein 224 of SARS-CoV-2, which is composed of two subunits S1 and S2. The binding effects can also involve other structural proteins, such as membrane (M) proteins 226, and possibly envelope (E) proteins and nucleocapsid (N) proteins. Generally, the nanometer gap size 209 can be selected based on binding effects with the biological material 222 or 230, which may include various membrane proteins on the surface of the biological material 222 or 230.

In another example, when the nanometer gap size 209 is selected to bind a biomarker 230, the binding effects can include binding effects with a macromolecule (e.g., a nucleic acid, protein, lipid, or the like). In one example, when the nanometer gap size 209 is selected to bind an antibody for a virus, the binding effects can include binding effects with one or more of a fragment antigen-binding region or a fragment crystallizable region.

In another aspect, the method can include coating at least one surface of an electrode gap region 207 with a first layer 213 including aptamers. The at least one surface can include one or more of a surface of the first electrode 204, the second electrode 206, or the channel 208, wherein the first electrode 204, the second electrode 206, and the channel 208 can each be adjacent to a substrate 202. In one example, the first layer 213 including aptamers can be directly adjacent to the at least one surface of an electrode gap region 207. In another example, the first layer 213 including aptamers may not be directly adjacent to the at least one surface of an electrode gap region 207. In this example, a second layer 211 including electrically-conductive solids can be directly adjacent to the at least one surface of an electrode gap region 207, and the first layer 213 including aptamers can be directly adjacent to the second layer 211. In one aspect, the electrically-conductive solids can be configured to bond with the aptamers. In another alternative, the electrode surfaces may be activated or functionalized in order to chemically react with and bond to the aptamers. For example, the aptamers may be bonded with an electrode by thiol functional groups on either the aptamer or the electrode surface. Successive layers of electrically-conductive solids can be attached to the aptamers by preparing the aptamers.

In one aspect, the first layer 213 including aptamers can include aptamers that can be functionalized to bind with a selected biological material. In one example, when the biological material is SARS-CoV-2, the aptamers can be functionalized to bind with the whole SARS-CoV-2 virus, with biomarkers for the SARS-CoV-2 virus, or with antibodies for the SARS-CoV-2 virus.

In another aspect, the aptamers can include a thiol end group configured to bind with gold electrodes. Thiol end groups bind with almost any materials. Thiol end groups are very aggressive and in some cases may cause corrosion of some metallic surfaces. In those cases other functional end groups with lower binding energies can be used such as, but not limited to, metal-carbon (e.g. carbene, acetylide, vinylidene, etc), metal-nitrogen (e.g. nitrene, etc), and the like.

In another aspect, the method can include coating the at least one surface with a second layer 211 including electrically-conductive solids that are configured to bond with the aptamers. The electrically-conductive solids can include at least one of carbon-based nanoparticles, metal nanoparticles, semiconductor nanoparticles, metal microbeads, semiconductor microbeads, the like, and combinations thereof.

In one aspect, the carbon-based nanoparticles can include one or more of: carbon nanotubes, graphene oxide, graphene quantum dots, the like, and combinations thereof. In another aspect, metal nanoparticles can include one or more of: iron oxide nanoparticles, gold nanoparticles, gold nanoshells, gold nanocages, silver nanoparticles, copper nanoparticles, platinum nanoparticles, the like, and combinations thereof. In another aspect, semiconductor nanoparticles can include one or more of: silicon nanoparticles, germanium nanoparticles, gallium arsenide nanoparticles, the like, and combinations thereof.

In another aspect, the metal microbeads can include one or more of: silver coated microbeads, steel-coated microbeads, gold-coated microbeads, the like, and combinations thereof. In another aspect, semiconductor microbeads can include one or more of: silicon microbeads, germanium microbeads, gallium arsenide microbeads, the like, and combinations thereof.

In another aspect, the method can include coating the electronic device 200a or 200b with additional alternating layers of the aptamers 217 and the electrically-conductive solids 215. The number of additional alternating layers can be selected to reach a nanometer gap size 209 between the first electrode 204 and the second electrode 206. As illustrated in FIGS. 2a and 2b, the first layer 213 including aptamers can be a monolayer having a thickness of one aptamer molecule, and the second layer including electrically-conductive solids 211 can be a monolayer having a thickness of one electrically-conductive solid particle.

Figure 3:
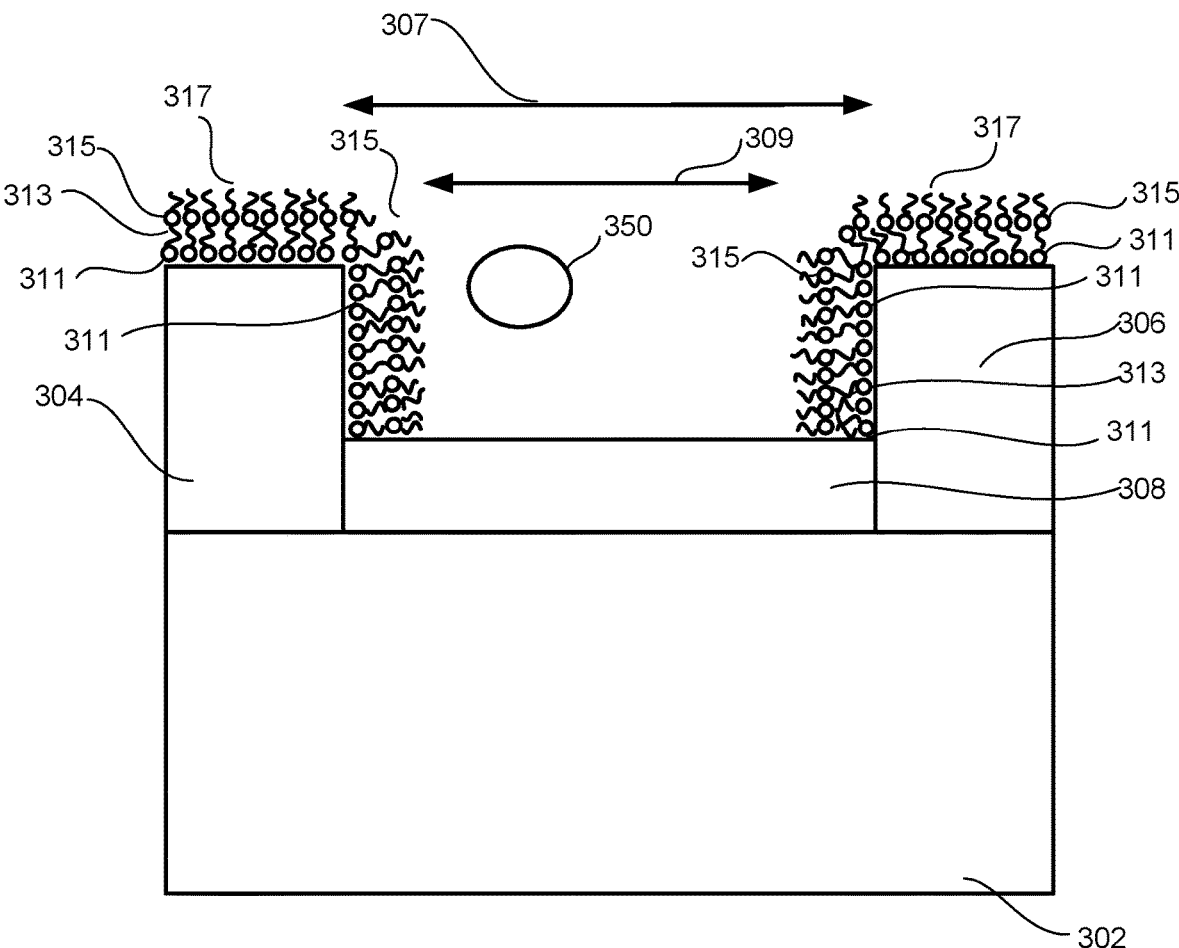
FIG. 3 is a side view illustrating an electronic device with a first layer including aptamers, a second layer including electrically-conductive solids, and an additional alternating layer in accordance with an example.

In another example, as illustrated in FIG. 3, an electronic device 300 can include a first electrode 304, a second electrode 306, and a channel 308, wherein each of the first electrode 304, the second electrode 306, and the channel 308 are adjacent to a substrate 302. The electronic device 300 can include a first electrode 304 including alternating layers of coated aptamers 313 and 317 and coated electrically-conductive solids 311 and 315. The electronic device 300 can include a second electrode 306 including alternating layers of coated aptamers 313 and 317 and coated electrically-conductive solids 311 and 315. The electronic device 300 can comprise a nanometer gap size 309 between the first electrode 304 and the second electrode 306. In one example, the nanometer gap size can be reduced from a larger gap size 307 by the alternating layers of the coated aptamers 313 and 317 and the coated electrically-conductive solids 311 and 315.

In one aspect, each layer 311, 313, 315, or 317 of the alternating layers of the coated aptamers 313 and 317 and the coated electrically-conductive solids 311 and 315 can be a monolayer including a thickness of a single molecule or a single particle, respectively.

In one aspect, the nanometer gap size can be less than: 1 μm, 900 nm, 800 nm, 700 nm, 600 nm, 500 nm, 450 nm, 400 nm, 350 nm, 300 nm, 250 nm, 200 nm, 150 nm, 100 nm, 75 nm, 50 nm, 35 nm, 20 nm, 15 nm, 10 nm, and 5 nm. In another aspect, the larger gap size can be greater than at least one of: 1 μm, 2 μm, 5 μm, 10 μm, 15 μm, 20 μm, 30 μm, 40 μm, 50 μm, 60 μm, 75 μm, 100 μm, 150 μm, 200 μm, 300 μm, 400 μm, and 500 μm. The nanometer gap size can be configured to selectively bind a biological material 350.

In one aspect, the electronic device 300 can be a micrometer-scale device that can be a sensor based on a field-effect transistor or an electron-tunneling device.

Figure 4:
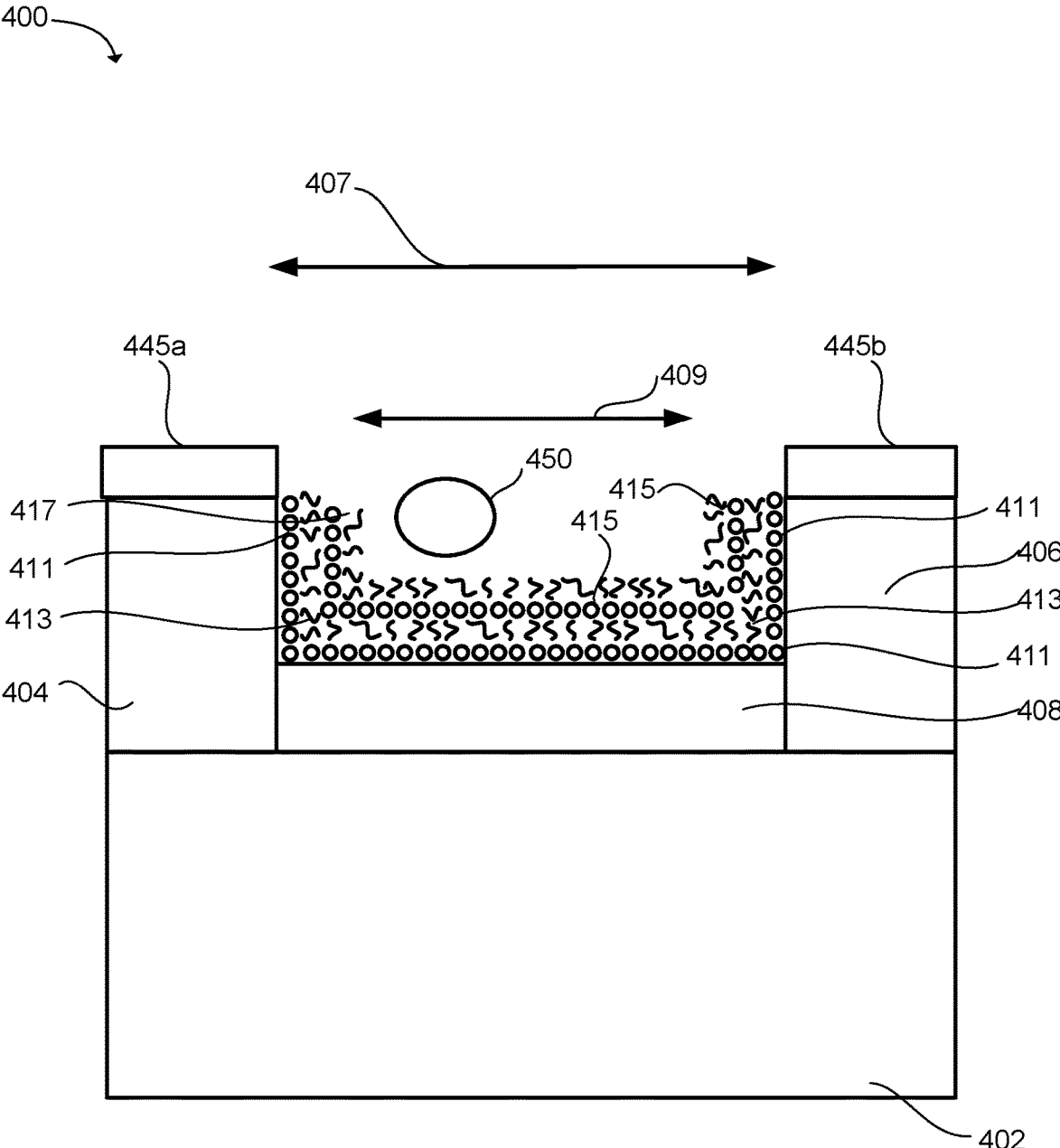
FIG. 4 is a side view illustrating an electronic device with a first layer including aptamers, a second layer including electrically-conductive solids, an additional alternating layer, and a hydrophobic layer in accordance with an example.

In another example, as illustrated in FIG. 4, an electronic device 400 can include a first electrode 404, a second electrode 406, and a channel 408, and a substrate 402. The electronic device 400 can include alternating layers of coated aptamers 413 and 417 and coated electrically-conductive solids 411 and 415. The electronic device 400 can comprise a nanometer gap size 409 that can be reduced from a larger gap size 407 by the alternating layers. The nanometer gap size can be configured to selectively bind a biological material 450.

In another aspect, the electronic device 400 can include a top insulating layer 445a and 445b of photoresist which can be hydrophobic. The photoresist can be patterned to cover the entire electronic device 400 except for the exposed active parts of the device which can be hydrophilic in order to facilitate deposition of aptamer on desired sensing surfaces and to improve performance during use.

Figure 5A:
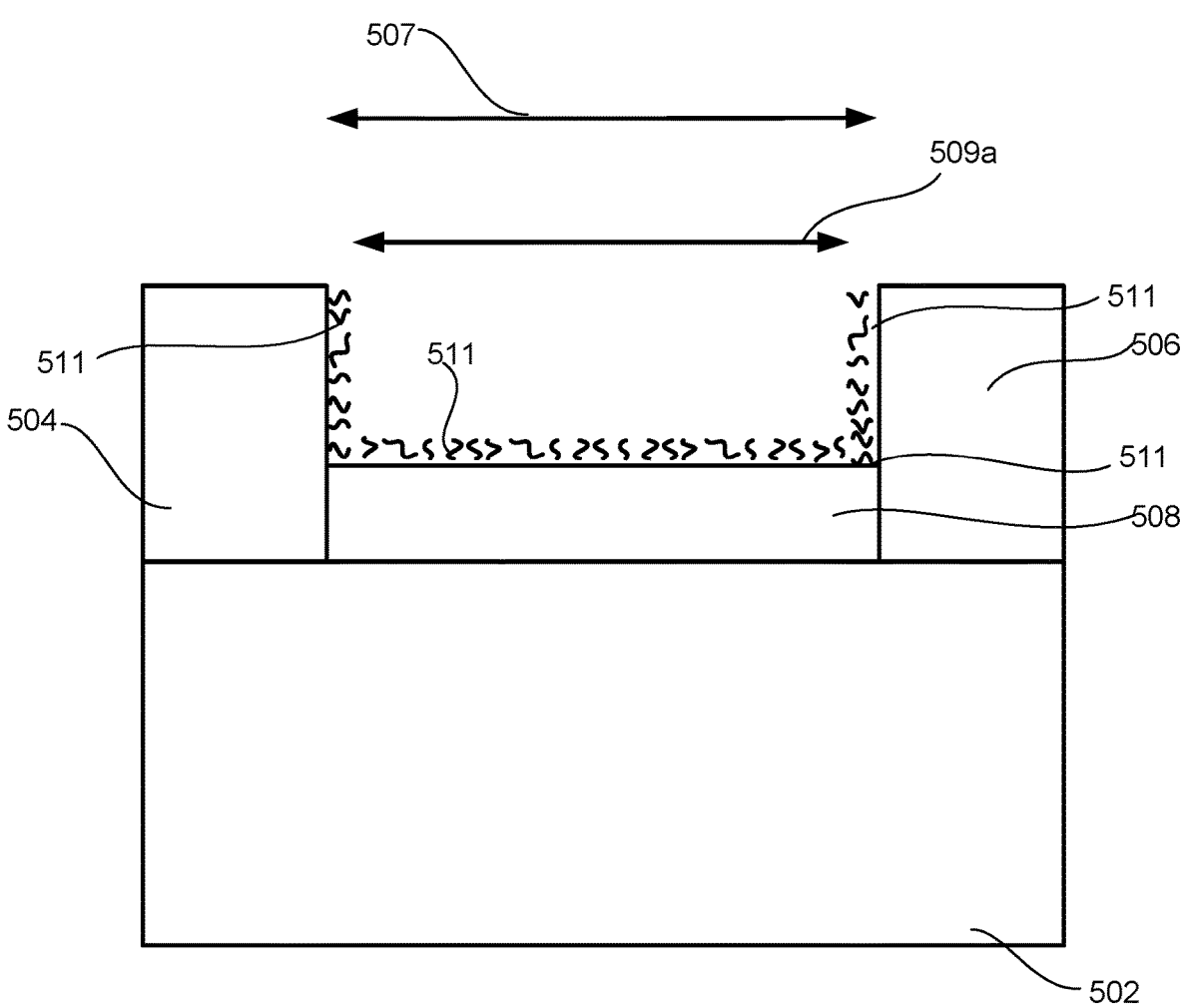
FIG. 5a is a side view illustrating a method for reducing electrode gap distances in an electronic device having a first electrode spatially separated from a second electrode by an electrode gap in accordance with an example.
Figure 5B:
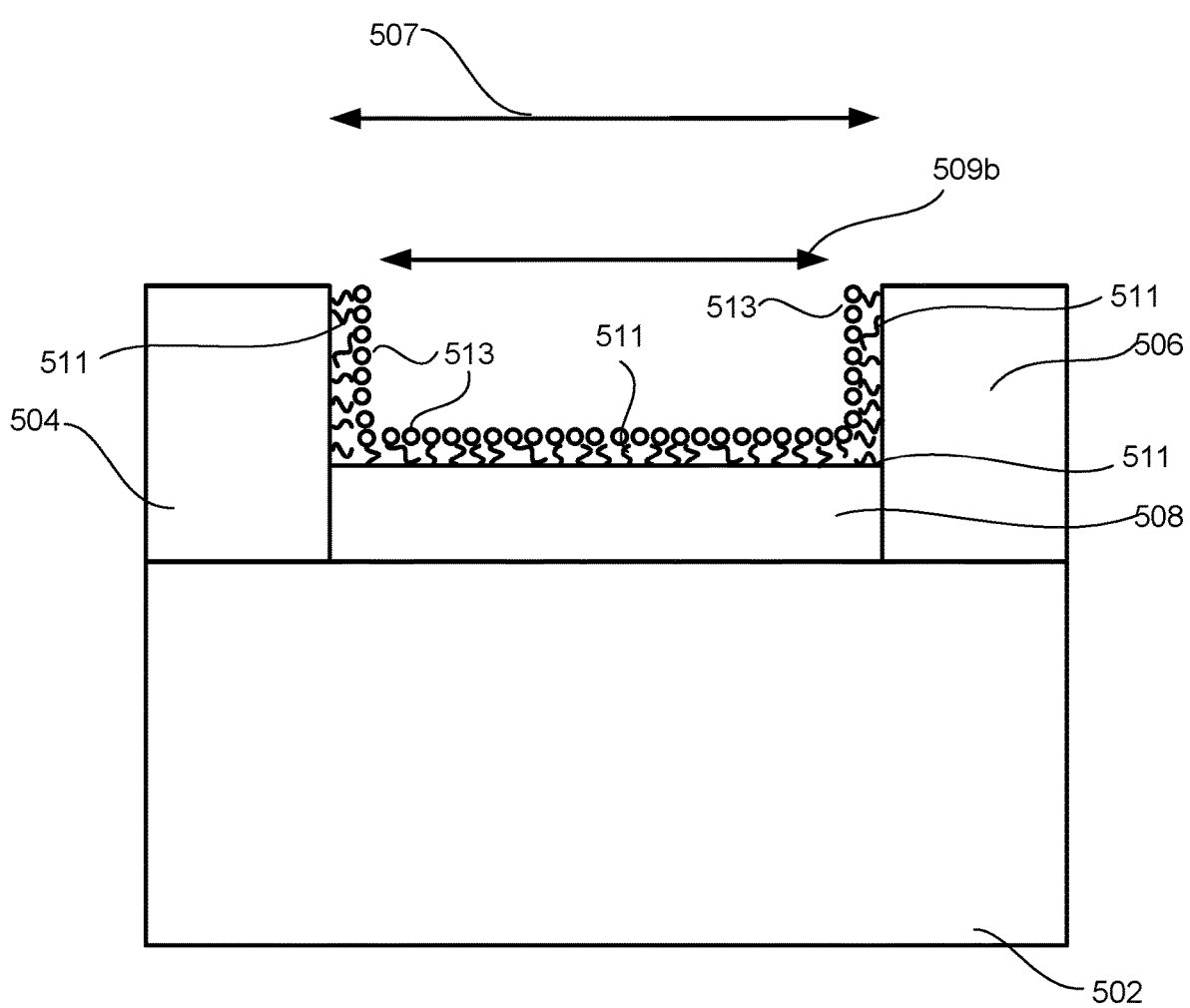
FIG. 5b is a side view illustrating a method for reducing electrode gap distances in an electronic device having a first electrode spatially separated from a second electrode by an electrode gap in accordance with an example.

In another example, as illustrated in FIGS. 5a-5d, a method for reducing electrode gap distances can be achieved in an electronic device 500a having a first electrode 504 spatially separated from a second electrode 506 by an electrode gap 507. In FIG. 5a, a channel can be adjacent to a substrate 502. The electrode gap 507 can be reduced to a gap size of 509a when a first surface of the electrode gap 507 region is coated with a first layer 511 including aptamers. In another aspect, as illustrated in FIG. 5b, the electrode gap 507 can be further reduced to a gap size of 509b when a first surface of the electrode gap 507 region is coated with a second layer 513 including electrically-conductive solids that are configured to bond with the aptamers.

Figure 5C:
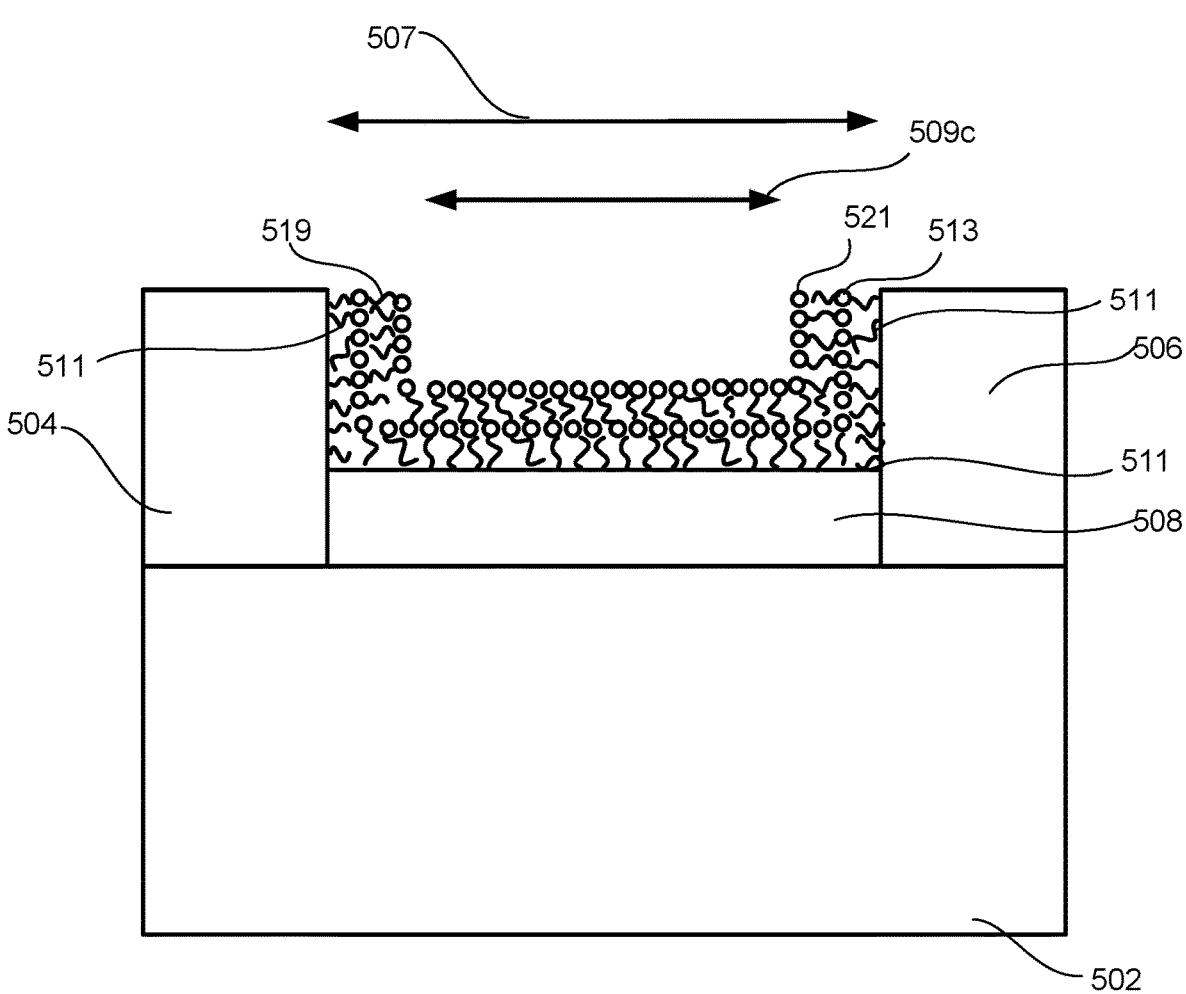
FIG. 5c is a side view illustrating a method for reducing electrode gap distances in an electronic device having a first electrode spatially separated from a second electrode by an electrode gap in accordance with an example.

In another aspect, as illustrated in FIG. 5c, the electrode gap 507 can be further reduced to a gap size of 509c when a first surface of the electrode gap 507 is coated with an additional alternating layer 519 of the aptamers and the electrically-conductive solids 521 to reach the nanometer gap size 509c between the first electrode 504 and the second electrode 506. In another aspect, as illustrated in FIG. 5d, the nanometer gap size 509d can be selected to bind a biological material 550.

Figure 6:
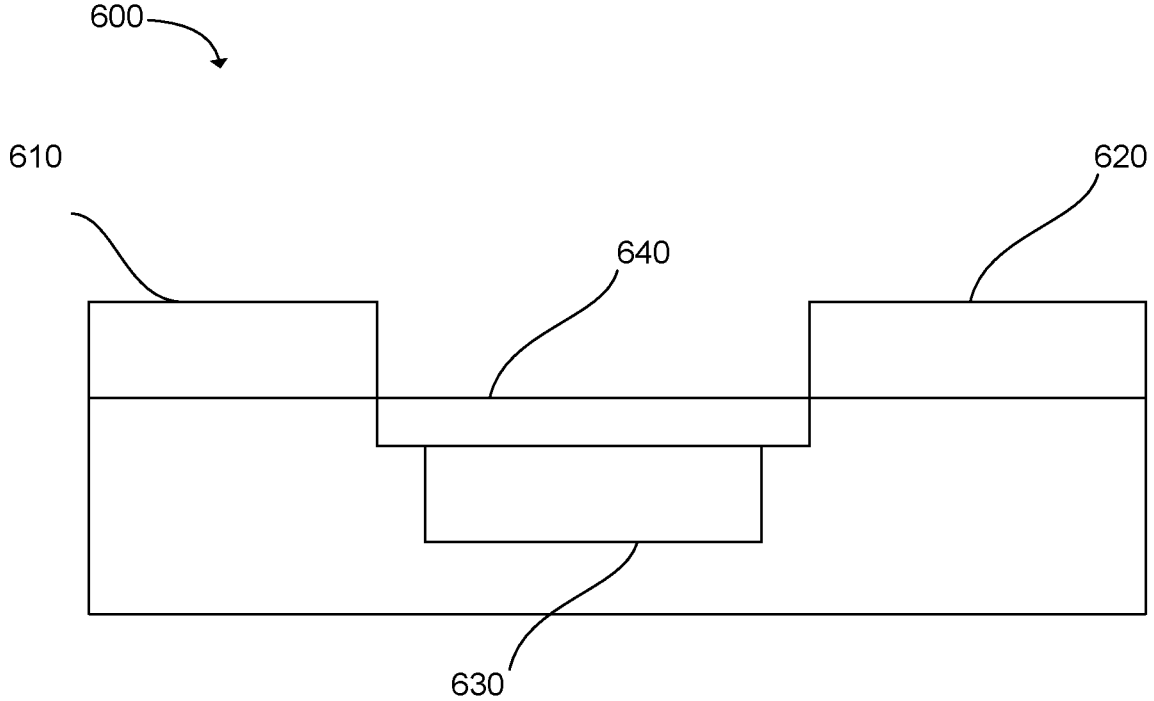
FIG. 6 is a side view illustrating a field effect transistor in accordance with an example.

In another example, as illustrated in FIG. 6, the electronic device can be a sensor based on a field effect transistor 600. The field effect transistor can include a source 610, a drain 620, a gate 630, and a gate dielectric 640 so as to form an insulated gate FET. In one example, the source 610 can be a first electrode, the drain 620 can be a second electrode, and the gate 630 can be a channel oriented between the first electrode and the second electrode.

Figure 7:
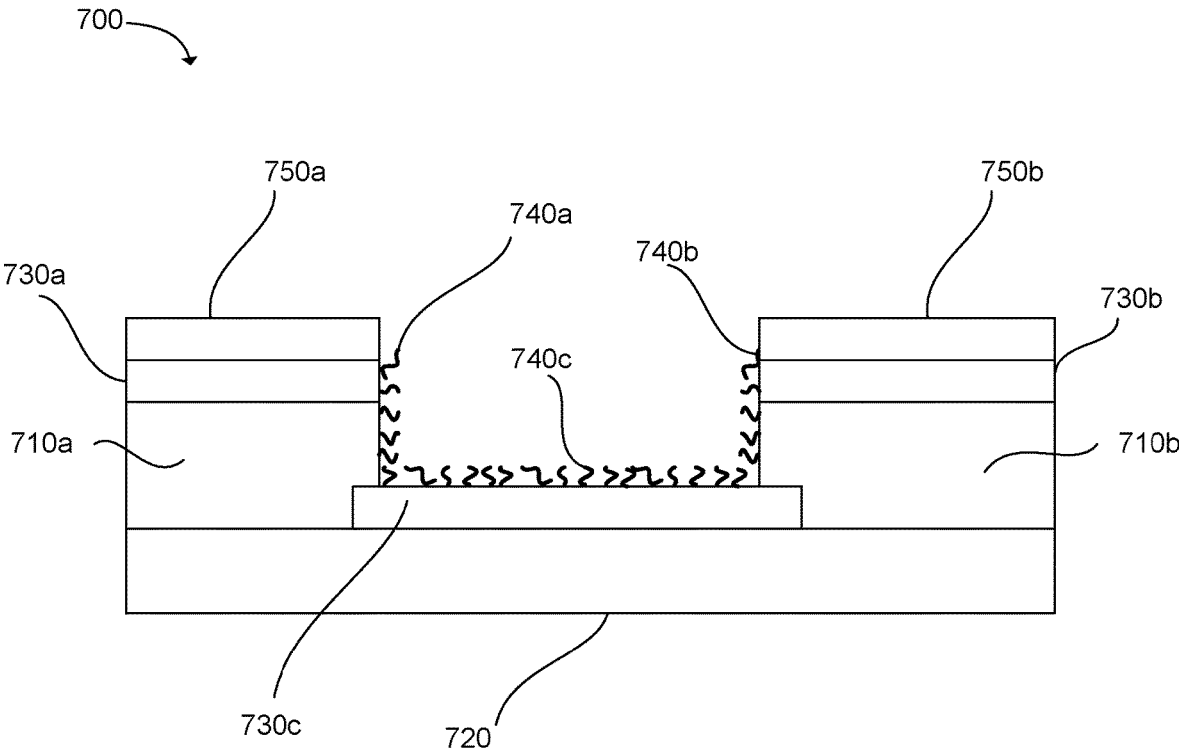
FIG. 7 is a side view illustrating an electron tunneling device in accordance with an example.

In another example, as illustrated in FIG. 7, the electronic device can be an electron tunneling device 700. In one aspect, the electron tunneling device 700 can include a substrate 720 (e.g., Si), a first electrode 710a (e.g., $SiO_2$), a second electrode 710b (e.g., $SiO_2$), a layer 710a, 710b, 710c of an electrically-conductive solid (e.g., gold), a layer of aptamers 740a, 740b, and 740c, and a hydrophobic material 750a and 750b (e.g., a layer of photoresist).

FIG. 8 illustrates a flow diagram of a method according to the present technology. For simplicity of explanation, the method is depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter.

In one example, a method 800 for reducing electrode gap distances in an electronic device having a first electrode spatially separated from a second electrode by an electrode gap is provided. The method can include selecting a nanometer gap size to bind a biological material based on a size of the biological material and binding effects with the biological material, as shown in block 810. The method can further include coating at least one surface of an electrode gap region with a first layer including aptamers, as shown in block 820. The method can further include coating the at least one surface with a second layer including electrically-conductive solids that are configured to bond with the aptamers, as shown in block 830. The method can further include coating the electronic device with additional alternating layers of the aptamers and the electrically-conductive solids to reach the nanometer gap size between a first electrode and a second electrode of the electronic device, as shown in block 840.

EXAMPLES

Example 1: Device Fabrication

Figure 9A:
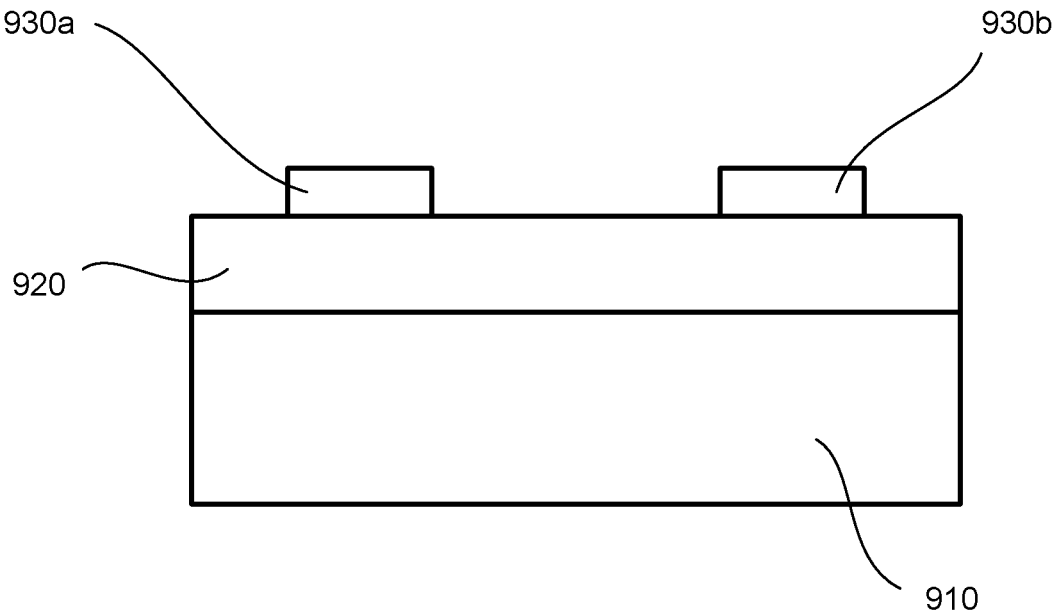
FIGS. 9a to 9d illustrate a fabrication process in accordance with an example.
Figure 9B:
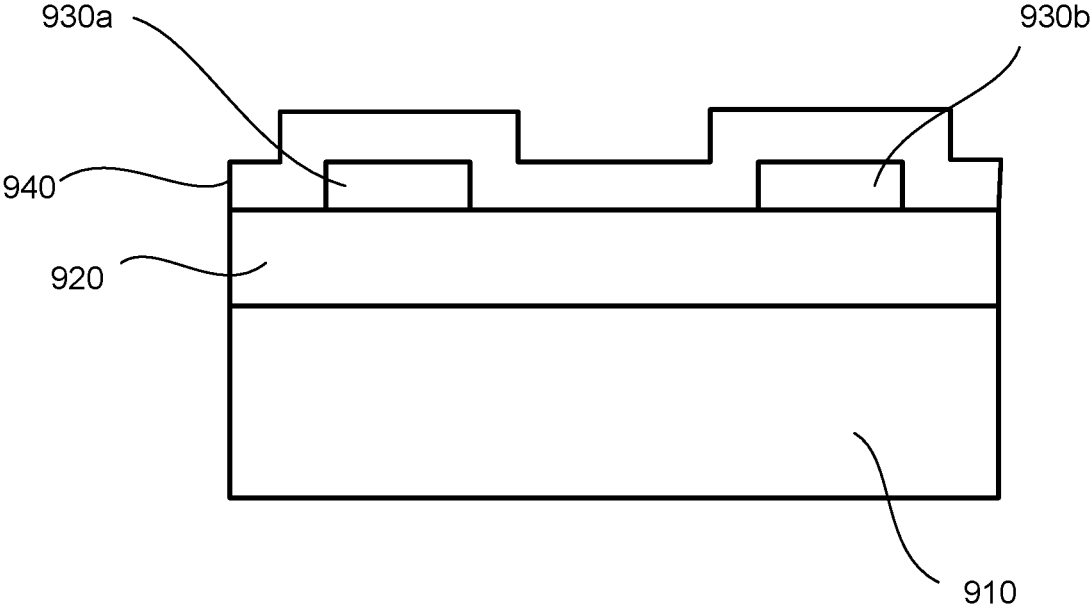
Figure 9C:
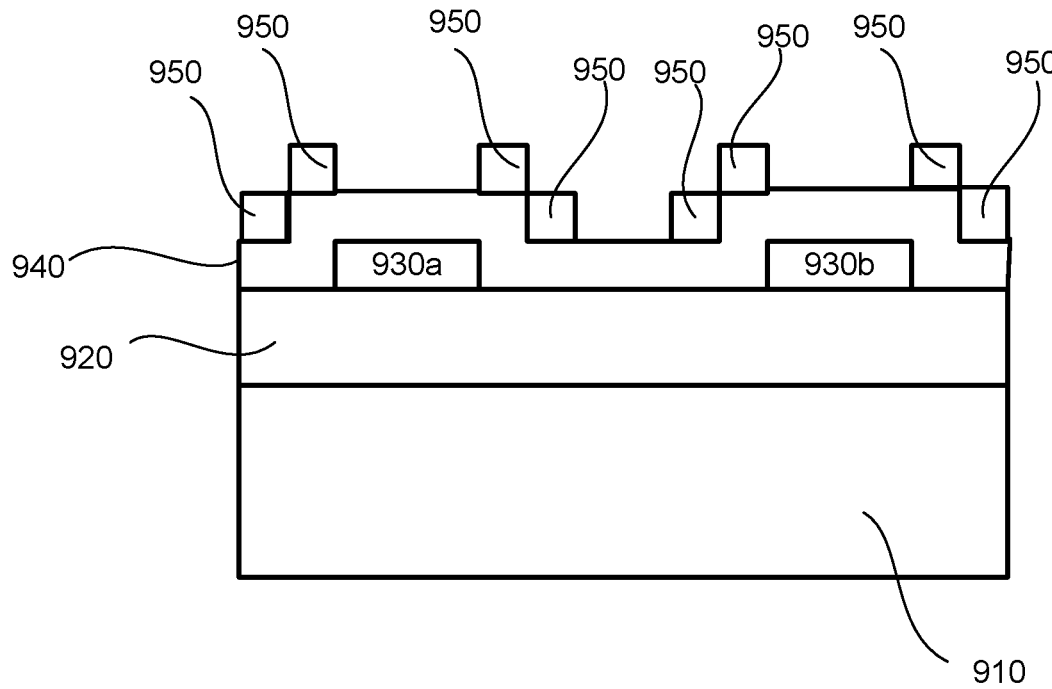
Figure 9D:
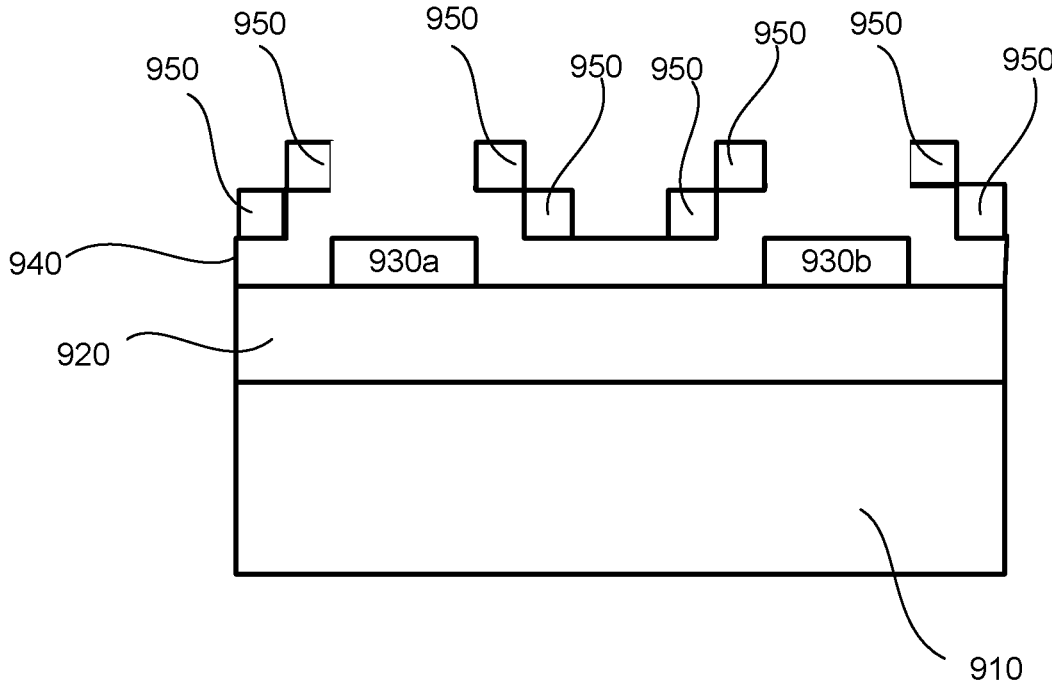

The fabrication process (FIGS. 9a to 9d) uses three masks. Deposition of 100 nm $Si_3N_4$ layer 920 on 4 inch Silicon 910 can be performed using low-pressure chemical vapor deposition (LPCVD) technique. The next operation is sputter deposition and patterning using Mask1 of the first Au/Cr layer (100 nm thick) 930a and 930b to form the bottom electrode and its pads for wire binding, as illustrated in FIG. 9a. The next operation is to deposit the spacer $SiO_2$ layer 940 using sputtering or the atomic layer deposition technique (for narrow gaps used in antibody and biomarker sensors), as illustrated in FIG. 9b followed by annealing at 400 degrees C. in forming gas. The spacer layer thickness is 70 nm for the CV2 virus, and 2-5 nm for biomarkers and the antibody. Next, the second Au/Cr layer (100 nm thick) 950 is sputtered and patterned using Mask2 to produce the top electrode and its connecting pads, as illustrated in FIG. 9c. The photoresist and the patterned Au/Cr layer are then used as a mask to dry etch the spacer $SiO_2$ layer to form the air gap, as illustrated in FIG. 9d. The last fabrication operation is to deposit a top insulating layer of photoresist (which is hydrophobic) and pattern it with Mask3 to cover the whole chip and expose the active parts of devices (which is hydrophilic) and the wire bonding pads. Gap distances in these spaces can then be adjusted by alternating layers of aptamer and gold particles as discussed previously.

Example 2: Field-Effect Transistor

An open channel FET consists of a recessed gate with the 10 nm atomic-layer deposited Hafnium dioxide ($HfO_2$) as the gate dielectric. The source, drain and gate electrodes are 100 nm-thick sputtered platinum. The channel length (distance between source and drain) is 1 μm. An open face channel with the embedded gate permits deposition of different channel materials to investigate the field effect on the channel materials that are exposed to the environment. The device geometry with its exposed channel region enables direct sensing of pathogen/gases/chemicals.

The chemo-resistive channel in the FETs are functionalized with aptamers that bind with viruses and provide selectivity to the sensor. In addition to the aptamers, sputtered Au films or zeolite molecular sieves can be used to immobilize the aptamers in the FET channel region, provide a medium for a virus to be trapped to bind with the aptamers, increase the channel conductivity to measurable values, and decrease the electrode gap distances between the source and the drain. The first FET is prepared using a sputtered thin gold film. The second type of FET devices are deposited with zeolite.

The channel in this case is n-type. Subsequently, deactivated CV2 was added to the aptamer-on-gold channel. The CV2 increases the channel conductance by a factor of ~10 at $V_{DS}$=2V. There is also a corresponding increase in the FET transconductance of about 5-fold at $V_{DS}$=2V.

The zeolite has micropores in its structure that can accommodate the aptamer and CV2 viruses and situate them in the FET channel region. The channel conductivity in this case increases from about 30-fold after adding aptamer and CV2. There is also a corresponding increase in the device transconductance of about 5-fold. The gate field effect is noticeable for positive $V_{DS}$.

Example 3: Quantum-Tunneling Current Sensor

The CV2 sensors in this example are composed of quantum-mechanical tunneling current sensors (TCS) functionalized with aptamers that bind with CV2 spiking proteins. Here arrays of these sensors are used as part of a multimodal sensor system. The biomarker and antibody sensors are also based on TCS and are functionalized with different aptamers that bind with specific biomarkers/antibodies. TCSs have single virus limit of detection (LOD) and a sensitivity as high as 95%. The whole virus sensor has a tunneling gap of 70 nm determined by the CV2 virus diameter of 125 nm. The biomarker/antibody sensors' tunneling gaps are smaller (about 1-5 nm) to match the length of molecules they sense.

The sensor array surface in this example is hydrophobic (a layer of photoresist can cap the whole chip except the sensor active channels and wiring pads) to guide the saliva to reside in the active hydrophilic channel (dry-etched $SiO_2$ and treated with oxygen plasma) of the sensors. The gold electrodes are treated with oxygen plasma to increase their binding energy with the thiol end group of the aptamers. TCS have excellent LOD/sensitivities and a machine learning software is developed to address device-device variations and sensor drift in biosensors.

Example 4: Quantum Tunneling Current Sensor

Figure 10A:
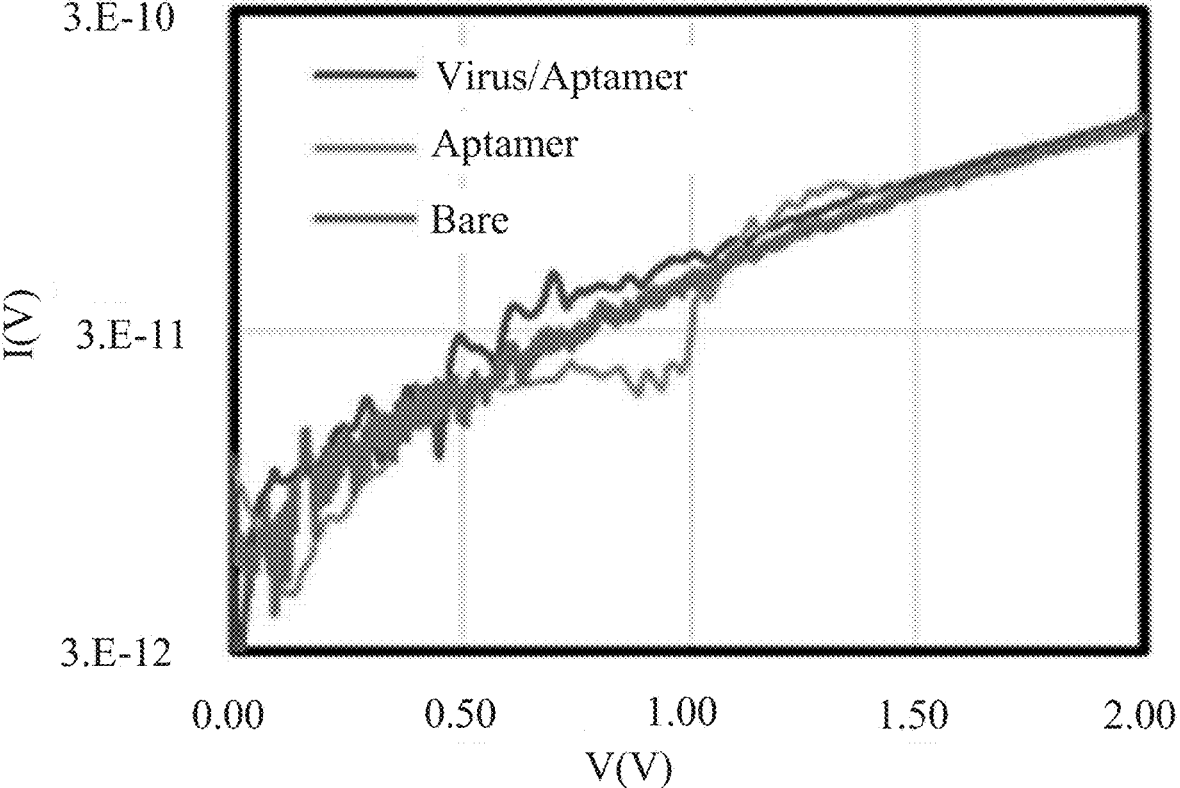
FIGS. 10a and 10b show current-voltage (I-Vs) and differential current-voltage (dI/dV) characteristics of the sensor with and without the aptamer/virus in accordance with an example.
Figure 10B:
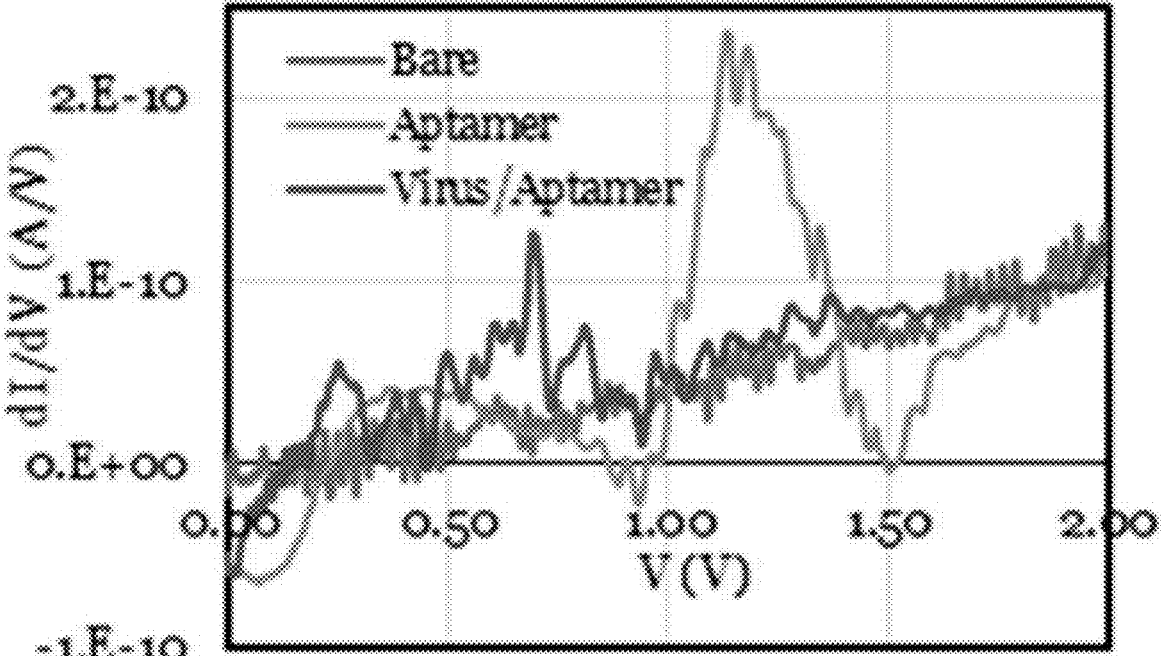
Figure 11A:
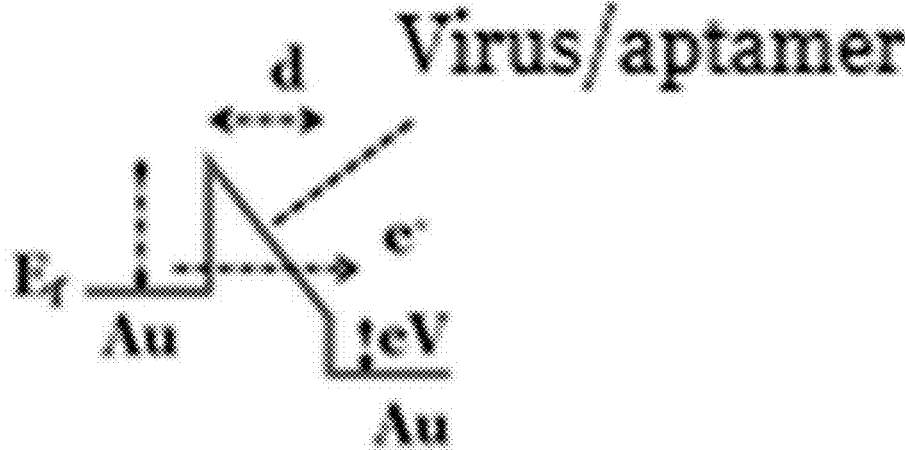
FIG. 11a to 11c illustrate a schematic of the current conduction mechanisms through the virus (or biomolecules) with different voltage and temperature dependences in accordance with an example.
Figure 11B:
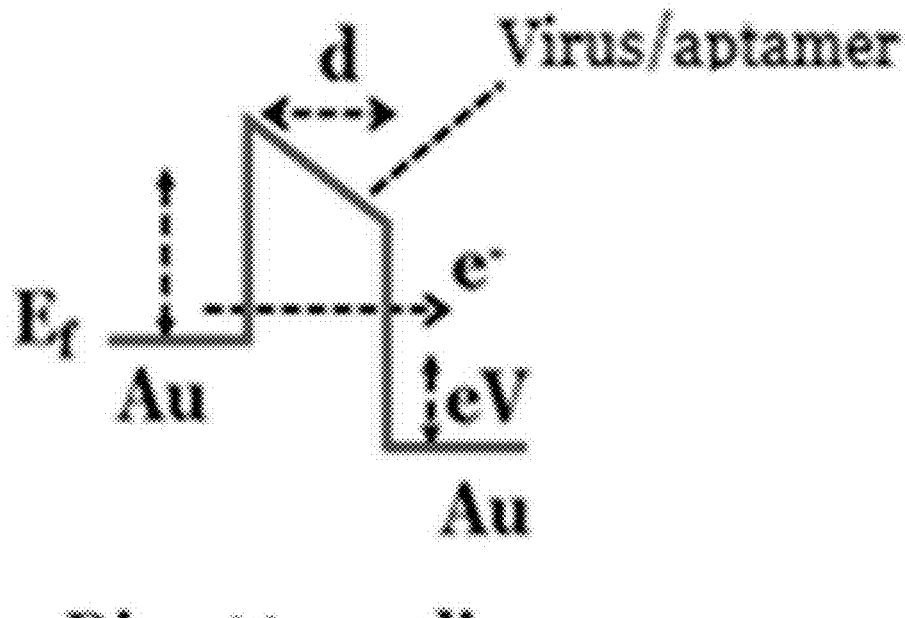
Figure 11C:
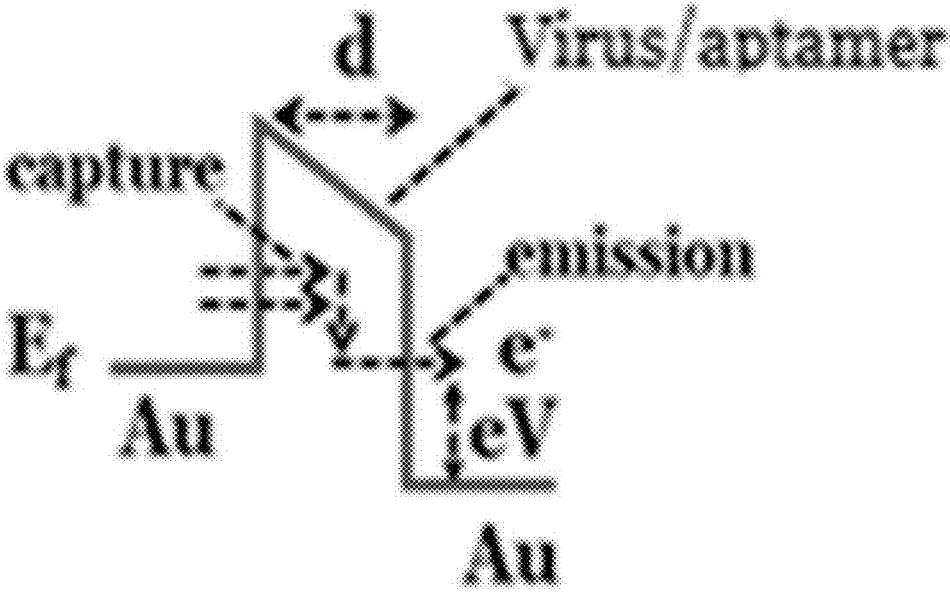
Figure 12A:
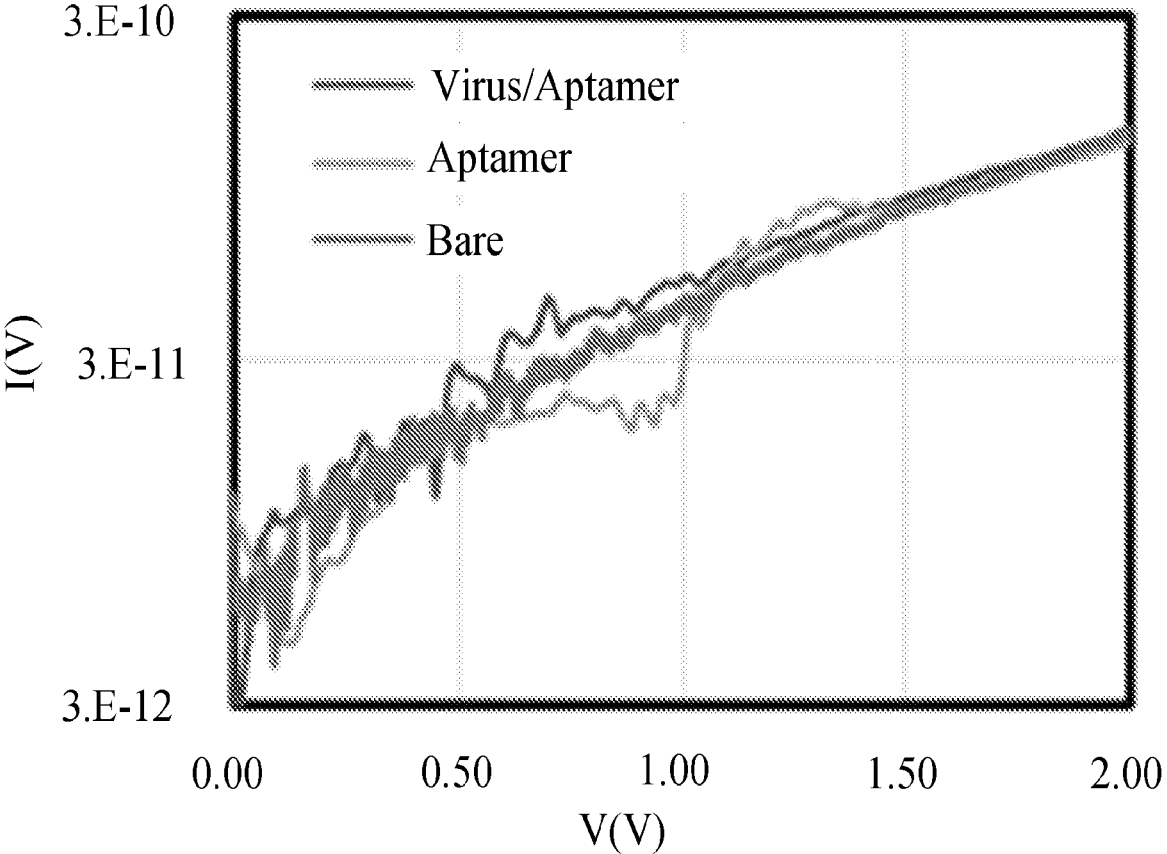
Figure 12B:
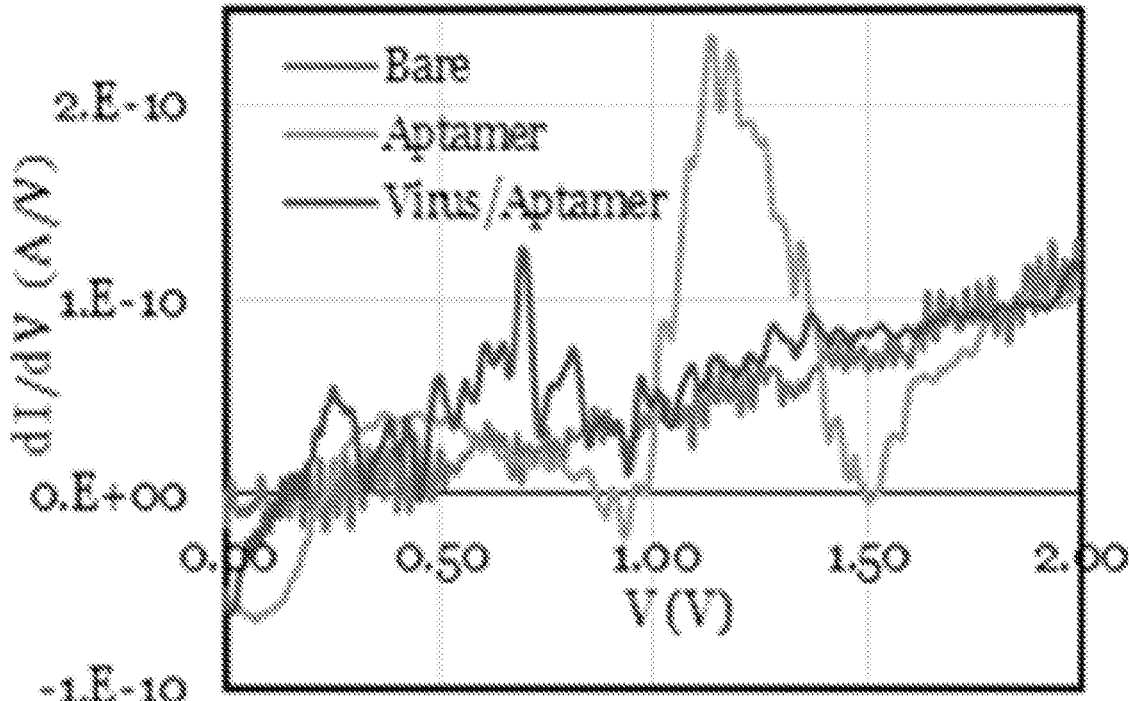
Figure 13A:
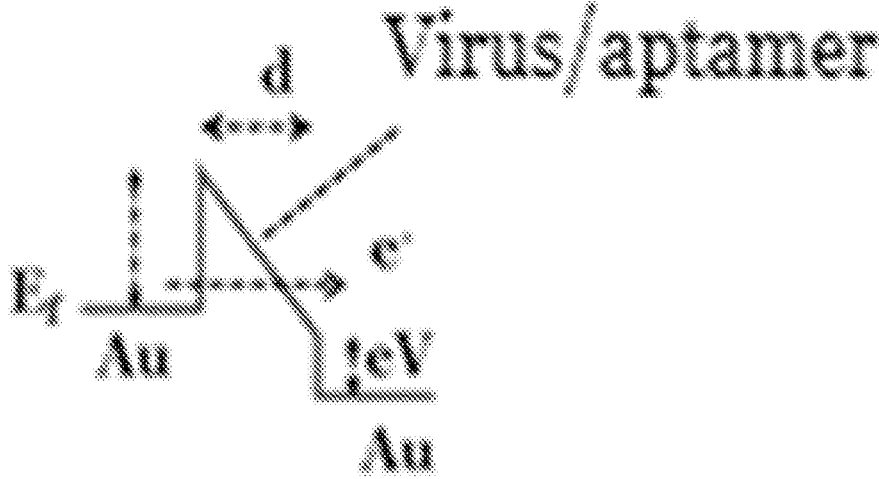
Figure 13B:
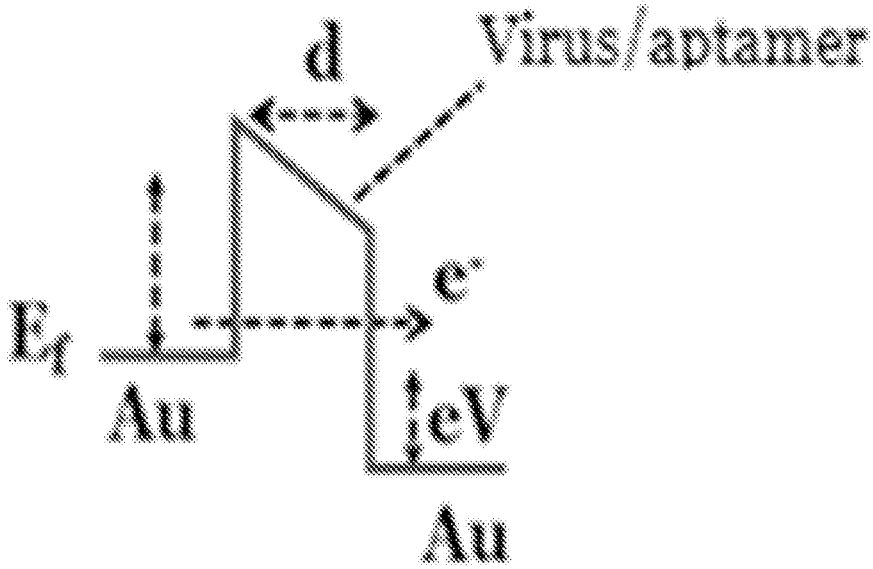
Figure 13C:
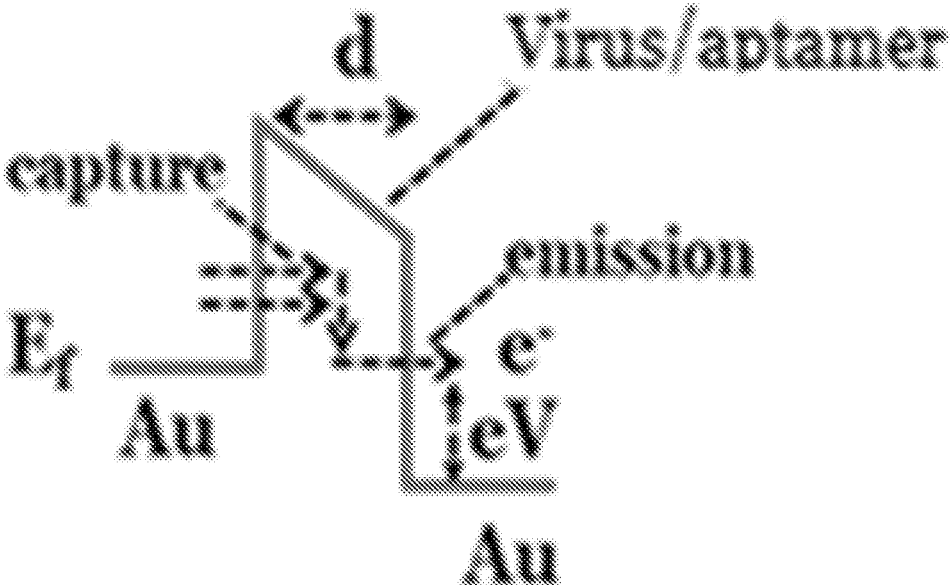

FIGS. 10a and 10b show I-Vs and differential current-voltage (dI/dV) characteristics of the sensor with and without the aptamer/virus. The current and differential current versus voltage characteristics of the tunneling gap device are uniquely determined by the effective band diagram (HOMO-LUMO) of the gold-aptamer-CV2-aptamer-gold device. The current conduction mechanisms through the virus (or biomolecules) are schematically shown in FIGS. 11a-11c with different voltage and temperature dependences. Given the large size of CV2, the current flow through multiple traps dominates.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method for reducing electrode gap distances in an electronic device having a first electrode spatially separated from a second electrode by an electrode gap, the method comprising:

selecting a nanometer gap size to bind a biological material based on a size of the biological material and binding effects with the biological material;

coating at least one surface of an electrode gap region with a first layer including molecular recognition groups;

coating the at least one surface with a second layer including electrically-conductive solids that are configured to bond with the molecular recognition groups, wherein the at least one surface is each of the first and second electrodes; and coating the electronic device with additional alternating layers of the molecular recognition groups and the electrically-conductive solids to reach the nanometer gap size between a first electrode and a second electrode of the electronic device.

2. The method of claim 1, wherein the biological material is one of a virus and a biomarker of the virus.

3. The method of claim 1, wherein the molecular recognition groups are configured to selectively bind with the biological material, and the molecular recognition groups are at least one of aptamers, antigens, and antibodies.

4. The method of claim 2, wherein the biological material is the virus and the method further comprising: selecting the nanometer gap size to bind a virus based on a size of the virus and binding effects with the virus.

5. The method of claim 4, wherein: the virus is selected from the group consisting of: Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronoviridae, Astroviridae, Bornaviridae, Arteriviridae, Hepeviridae, Retroviridae, Calimoviridae, Hepadnasviridae, and combinations thereof, or the virus is a subviral agent selected from the group consisting of: viroids, satellites, defective interfering particles, prions, and combinations thereof.

6. The method of claim 4, further comprising: selecting the nanometer gap size to bind the virus based on the size of the virus wherein the size of the virus is less than at least one of: 500 nm, 400 nm, 300 nm, 200 nm, 100 nm, 50 nm, 20 nm, and 15 nm.

7. The method of claim 2, wherein the biological material is the biomarker and the method further comprising:
selecting the nanometer gap size to bind the biomarker of the virus based on the size of the biomarker and binding effects with the biomarker, wherein the biomarker has a biomarker size of less than at least one of 10 nm, 5 nm, 2 nm, and 1 nm.

8. The method of claim 7, wherein the biomarker is an antibody for the virus.

9. The method of claim 1, further comprising:
coating the electronic device with the additional alternating layers to reach the nanometer gap size less than at least one of: 100 nm, 10 nm, and 5 nm.

10. The method of claim 1, wherein the electrode gap before coating is greater than 1 μm.

11. The method of claim 1, wherein the at least one surface further includes a channel surface oriented between the first and second electrodes.

12. The method of claim 1, wherein the first and second layers are monolayers having a thickness of a single particle or a single molecule.

13. The method of claim 1, wherein the electrically conductive solids include at least one of: carbon-based nanoparticles, metal nanoparticles, semiconductor nanoparticles, metal microbeads, semiconductor microbeads, and combinations thereof.

14. The method of claim 13, wherein the electrically conductive solids include at least one of: gold nanoparticles, silver nanoparticles, palladium nanoparticles, platinum nanoparticles, and combinations thereof.

15. The method of claim 1, wherein the electronic device is a sensor based on a field-effect transistor or an electron tunneling device.

16. A micrometer-scale device comprising:
a first electrode coated with alternating layers of molecular recognition groups and electrically-conductive solids;
a second electrode coated with alternating layers of molecular recognition groups and electrically-conductive solids; and
a nanometer gap size between the first electrode and the second electrode, wherein the nanometer gap size is reduced by each of the alternating layers of the molecular recognition groups and the electrically-conductive solids.

17. The micrometer-scale device of claim 16, wherein each layer of the alternating layers of the molecular recognition groups and the electrically-conductive solids is a monolayer including a thickness having a single particle.

18. The micrometer-scale device of claim 16, wherein the nanometer gap size less than at least one of: 1 μm, 500 nm, 400 nm, 300 nm, 200 nm, 100 nm, 50 nm, 20 nm, 10 nm, 5 nm, 2 nm, and 1 nm.

19. The micrometer-scale device of claim 16, wherein the gap size is greater than 1 μm.

20. The micrometer-scale device of claim 16, wherein the molecular recognition groups are selected to bind with at least one of a virus and a biomarker, and are at least one of an aptamer, an antibody, and an antigen.

21. The micrometer-scale device of claim 16, wherein the electrically-conductive solids include at least one of: carbon-based nanoparticles, metal nanoparticles, semiconductor nanoparticles, metal microbeads, semiconductor microbeads, and combinations thereof.

22. The micrometer-scale device of claim 16, wherein the electrically conductive solids include at least one of: gold nanoparticles, silver nanoparticles, palladium nanoparticles, platinum nanoparticles, and combinations thereof.

23. The micrometer-scale device of claim 16, wherein the micrometer-scale device is a sensor based on a field-effect transistor or an electron tunneling device.

*     *     *     *     *